(12) United States Patent
Flaherty et al.

(10) Patent No.: US 7,018,360 B2
(45) Date of Patent: Mar. 28, 2006

(54) FLOW RESTRICTION SYSTEM AND METHOD FOR PATIENT INFUSION DEVICE

(75) Inventors: J. Christopher Flaherty, Topsfield, MA (US); John T. Garibotto, Charlestown, MA (US); William Gorman, South Hamilton, MA (US); Timothy J. Wood, Wilminton, MA (US); Richard Morgan Moroney, III, Princeton, NJ (US)

(73) Assignee: Insulet Corporation, Bedford, MA (US)

( * ) Notice: Subject to any disclaimer, the term of this patent is extended or adjusted under 35 U.S.C. 154(b) by 169 days.

(21) Appl. No.: 10/198,690

(22) Filed: Jul. 16, 2002

(65) Prior Publication Data

US 2004/0015131 A1    Jan. 22, 2004

(51) Int. Cl.
*A61M 1/00* (2006.01)

(52) U.S. Cl. .................................................... 604/123

(58) Field of Classification Search ............... 604/30, 604/33, 34, 122–125, 250, 65–67, 131, 93.01, 604/890.1–892.1, 288.01–288.04, 127, 246, 604/134, 135
See application file for complete search history.

(56) References Cited

U.S. PATENT DOCUMENTS

| | | | |
|---|---|---|---|
| 3,631,847 A | 1/1972 | Hobbs | |
| 3,812,843 A | 5/1974 | Wootten et al. | |
| 3,885,662 A | 5/1975 | Schaefer | |
| 4,067,000 A | 1/1978 | Carlson | |
| 4,108,177 A | 8/1978 | Pistor | |
| 4,151,845 A | 5/1979 | Clemens | |
| 4,193,397 A | 3/1980 | Tucker et al. | |
| 4,211,998 A | 7/1980 | Junginger et al. | |
| 4,231,019 A | 10/1980 | Junginger et al. | |
| 4,268,150 A | 5/1981 | Chen | |
| 4,364,385 A | 12/1982 | Lossef | |
| 4,373,527 A | 2/1983 | Fischell | |
| 4,424,720 A | 1/1984 | Bucchianeri | |

(Continued)

FOREIGN PATENT DOCUMENTS

DE    4200595    7/1993

(Continued)

OTHER PUBLICATIONS

Web-Site Brochure dated Jan. 4, 2000. MiniMed 508. "Doing its job. Naturally." www.minimed.com/tiles/mm_113.htm.

(Continued)

*Primary Examiner*—Nicholas D. Lucchesi
*Assistant Examiner*—Matthew F. DeSanto

(57) ABSTRACT

A device for delivering fluid, such as insulin for example, to a patient. The device includes a flow path having an exit port assembly adapted to connect to a transcutaneous patient access tool, and a reservoir connected to the exit port assembly. The device also includes a flow restriction system having an air removal filter communicating with the flow path and allowing air to exit the flow path and preventing fluid from exiting the flow path, and a flow restrictor positioned within the flow path between the air removal filter and the exit port assembly. Among other features and advantages, the flow restriction system of the present invention allows the flow path of the fluid delivery device to be purged of air, or "primed" prior to operation, such that desired volumes of fluid can be accurately delivered by the device.

9 Claims, 12 Drawing Sheets

U.S. PATENT DOCUMENTS

| | | | |
|---|---|---|---|
| 4,435,173 A | 3/1984 | Siposs et al. | |
| 4,469,481 A | 9/1984 | Kobayashi | |
| 4,475,901 A | 10/1984 | Kraegen et al. | |
| 4,498,843 A | 2/1985 | Schneider et al. | |
| 4,507,115 A | 3/1985 | Kambara et al. | |
| 4,514,732 A | 4/1985 | Hayes, Jr. | |
| 4,529,401 A | 7/1985 | Leslie et al. | |
| 4,551,134 A | 11/1985 | Slavik et al. | |
| 4,559,033 A | 12/1985 | Stephen et al. | |
| 4,559,037 A | 12/1985 | Franetzki et al. | |
| 4,560,979 A | 12/1985 | Rosskopf | |
| 4,562,751 A | 1/1986 | Nason et al. | |
| 4,585,439 A | 4/1986 | Michel | |
| 4,601,707 A | 7/1986 | Albisser et al. | |
| 4,624,661 A | 11/1986 | Arimond | |
| 4,634,427 A | 1/1987 | Hannula et al. | |
| 4,678,408 A | 7/1987 | Nason et al. | |
| 4,684,368 A | 8/1987 | Kenyon | |
| 4,685,903 A | 8/1987 | Cable et al. | |
| 4,734,092 A | 3/1988 | Millerd | |
| 4,743,243 A * | 5/1988 | Vaillancourt | 604/405 |
| 4,755,173 A | 7/1988 | Konopka et al. | |
| 4,781,688 A | 11/1988 | Thoma et al. | |
| 4,781,693 A | 11/1988 | Martinez et al. | |
| 4,801,957 A | 1/1989 | Vandemoere | |
| 4,808,161 A | 2/1989 | Kamen | |
| 4,836,752 A | 6/1989 | Burkett | |
| D303,013 S | 8/1989 | Konopka | |
| 4,855,746 A | 8/1989 | Stacy | |
| 4,871,351 A * | 10/1989 | Feingold | 604/66 |
| 4,882,600 A | 11/1989 | Van de Moere | |
| 4,886,499 A | 12/1989 | Cirelli et al. | |
| 4,898,579 A | 2/1990 | Groshong et al. | |
| D306,691 S | 3/1990 | Aran | |
| 4,944,659 A | 7/1990 | Labbe et al. | |
| D311,735 S | 10/1990 | Arai et al. | |
| 4,969,874 A | 11/1990 | Michel et al. | |
| 4,973,998 A | 11/1990 | Gates | |
| 4,981,464 A * | 1/1991 | Suzuki | 604/415 |
| D315,727 S | 3/1991 | Arai et al. | |
| 5,007,458 A | 4/1991 | Marcus et al. | |
| 5,045,871 A | 9/1991 | Reinholdson | |
| 5,062,841 A | 11/1991 | Siegel | |
| 5,109,850 A | 5/1992 | Blanco et al. | |
| 5,125,415 A * | 6/1992 | Bell | 600/579 |
| 5,176,662 A | 1/1993 | Bartholomew et al. | |
| 5,178,609 A | 1/1993 | Ishikawa | |
| 5,205,819 A | 4/1993 | Ross et al. | |
| 5,213,483 A | 5/1993 | Flaherty et al. | |
| 5,232,439 A | 8/1993 | Campbell et al. | |
| 5,239,326 A | 8/1993 | Takai | |
| 5,242,406 A | 9/1993 | Gross et al. | |
| 5,244,463 A | 9/1993 | Cordner, Jr. et al. | |
| 5,245,447 A | 9/1993 | Stemmle | |
| 5,254,096 A | 10/1993 | Rondelet et al. | |
| 5,257,980 A | 11/1993 | Van Antwerp et al. | |
| 5,281,202 A | 1/1994 | Weber et al. | |
| 5,308,335 A * | 5/1994 | Ross et al. | 604/141 |
| 5,312,337 A | 5/1994 | Flaherty et al. | |
| 5,318,540 A | 6/1994 | Athayde et al. | |
| 5,342,313 A | 8/1994 | Campbell et al. | |
| 5,346,476 A * | 9/1994 | Elson | 604/135 |
| 5,364,342 A | 11/1994 | Beuchat et al. | |
| 5,411,480 A | 5/1995 | Kriesel | |
| 5,433,710 A | 7/1995 | Van Antwerp et al. | |
| 5,452,033 A | 9/1995 | Balling et al. | |
| 5,492,534 A | 2/1996 | Athayde et al. | |
| 5,505,709 A | 4/1996 | Funderburk et al. | |
| 5,507,288 A | 4/1996 | Böcker et al. | |
| 5,514,096 A | 5/1996 | Hiejima | |
| 5,533,389 A | 7/1996 | Kamen et al. | |
| 5,545,152 A | 8/1996 | Funderburk et al. | |
| 5,575,770 A | 11/1996 | Melsky et al. | |
| 5,576,781 A | 11/1996 | Deleeuw | |
| 5,582,593 A | 12/1996 | Hultman | |
| 5,584,813 A | 12/1996 | Livingston et al. | |
| 5,630,710 A | 5/1997 | Tune et al. | |
| 5,637,095 A | 6/1997 | Nason et al. | |
| 5,643,213 A | 7/1997 | McPhee | |
| 5,647,853 A | 7/1997 | Feldmann et al. | |
| 5,660,728 A | 8/1997 | Saaski et al. | |
| 5,665,065 A | 9/1997 | Colman et al. | |
| 5,665,070 A | 9/1997 | McPhee | |
| 5,695,490 A | 12/1997 | Flaherty et al. | |
| 5,702,363 A | 12/1997 | Flaherty | |
| 5,704,520 A | 1/1998 | Gross | |
| 5,726,404 A | 3/1998 | Brody | |
| 5,726,751 A | 3/1998 | Altendorf et al. | |
| 5,741,228 A | 4/1998 | Lambrecht et al. | |
| 5,747,350 A | 5/1998 | Sattler | |
| 5,748,827 A | 5/1998 | Holl et al. | |
| 5,755,682 A | 5/1998 | Knudson et al. | |
| 5,776,103 A | 7/1998 | Kriesel et al. | |
| 5,779,676 A | 7/1998 | Kriesel et al. | |
| 5,785,681 A | 7/1998 | Indravudh | |
| 5,785,688 A | 7/1998 | Joshi et al. | |
| 5,797,881 A | 8/1998 | Gadot | |
| 5,800,397 A | 9/1998 | Wilson et al. | |
| 5,800,405 A | 9/1998 | McPhee | |
| 5,810,015 A | 9/1998 | Flaherty | |
| 5,814,020 A | 9/1998 | Gross | |
| 5,839,467 A | 11/1998 | Saaski et al. | |
| 5,840,063 A | 11/1998 | Flaherty | |
| 5,845,218 A | 12/1998 | Altschul | |
| 5,848,991 A | 12/1998 | Gross et al. | |
| 5,851,197 A | 12/1998 | Marano et al. | |
| 5,858,005 A | 1/1999 | Kriesel | |
| D405,524 S | 2/1999 | Falk et al. | |
| 5,875,393 A | 2/1999 | Altschul et al. | |
| 5,886,647 A | 3/1999 | Badger et al. | |
| 5,891,097 A | 4/1999 | Saito et al. | |
| 5,897,530 A | 4/1999 | Jackson | |
| 5,906,597 A | 5/1999 | McPhee | |
| 5,911,716 A | 6/1999 | Rake et al. | |
| 5,919,167 A | 7/1999 | Mulhauser et al. | |
| 5,931,814 A | 8/1999 | Alex et al. | |
| 5,935,099 A | 8/1999 | Peterson et al. | |
| 5,954,058 A | 9/1999 | Flaherty | |
| 5,957,890 A | 9/1999 | Mann et al. | |
| 5,961,492 A | 10/1999 | Kriesel et al. | |
| 5,965,848 A | 10/1999 | Altschul et al. | |
| 5,983,094 A | 11/1999 | Altschul et al. | |
| 5,993,423 A | 11/1999 | Choi | |
| 5,997,501 A | 12/1999 | Gross et al. | |
| 6,019,747 A | 2/2000 | McPhee | |
| 6,024,539 A | 2/2000 | Blomquist | |
| 6,045,533 A * | 4/2000 | Kriesel et al. | 604/132 |
| 6,061,580 A | 5/2000 | Altschul et al. | |
| 6,071,292 A | 6/2000 | Makower et al. | |
| 6,126,637 A * | 10/2000 | Kriesel et al. | 604/132 |
| 6,144,847 A | 11/2000 | Altschul et al. | |
| 6,152,898 A | 11/2000 | Olsen | |
| 6,174,300 B1 | 1/2001 | Kriesel et al. | |
| 6,190,359 B1 | 2/2001 | Heruth | |
| 6,206,850 B1* | 3/2001 | O'Neil | 604/80 |
| 6,363,609 B1 | 4/2002 | Pickren | |
| 6,375,638 B1 | 4/2002 | Nason et al. | |
| 6,520,936 B1 | 2/2003 | Mann | |
| 6,527,744 B1 | 3/2003 | Kriesel et al. | |
| 6,537,249 B1* | 3/2003 | Kriesell et al. | 604/131 |

FOREIGN PATENT DOCUMENTS

| | | |
|---|---|---|
| DE | 19920896 | 9/2000 |
| EP | 0342947 | 5/1989 |
| EP | 0763369 | 3/1997 |
| EP | 0867196 | 3/1998 |
| EP | 0937475 | 8/1999 |
| WO | WO81/01658 | 6/1981 |
| WO | WO86/06796 | 11/1986 |
| WO | WO98/00193 | 1/1998 |
| WO | WO98801071 | 1/1998 |
| WO | WO99/10040 | 3/1999 |
| WO | WO00/19887 | 9/1999 |
| WO | WO99/56803 | 11/1999 |
| WO | WO99/62576 | 12/1999 |
| WO | WO0010628 | 3/2000 |
| WO | WO00/29047 | 5/2000 |
| WO | WO00/29049 | 5/2000 |
| WO | WO00/74752 | 5/2000 |
| WO | WO00/30705 | 6/2000 |
| WO | WO00/78210 | 6/2000 |
| WO | WO00/48112 | 8/2000 |
| WO | WO00/61215 | 10/2000 |
| WO | WO01/52727 | 1/2001 |
| WO | WO01/5663 | 8/2001 |
| WO | WO01/76684 | 10/2001 |
| WO | WO02/20073 | 3/2002 |
| WO | WO02/26282 | 4/2002 |

OTHER PUBLICATIONS

Web-Site Brochure dated Dec. 20, 1999. Applied Medical Technology. "508 Pump Information", www.applied-medical.co.uk/508.htm.

Web-Site Brochure dated Jan. 4, 2000. "The Glucose Sensor". www.animascorp.com/sensor_f.html.

Web-Site Brochure dated Dec. 20, 1999. "The Animas R-1000 Insulin Pump". www.animascorp.com/pump_f_s.html.

Web-Site Brochure dated Dec. 20, 1999. "The Animas R-1000 Insulin Pump". www.animascorp.com/pump_f_f.html.

Web-Site Brochure dated Jan. 4, 2000. SOOIL-Homepage. "Portable Insulin Pump". www.sooil.com/intro2.htm.

Web-Site Brochure dated Jan. 4, 2000. SOOIL-Homepage. "Portable Insulin Pump". www.sooil.com/product2.htm.

Web-Site Brochure dated Jan. 4, 2000. SOOIL-Homepage. "Portable Insulin Pump". www.sooil.com/product3.htm.

Web-Site Brochure dated Jan. 4, 2000. SOOIL-Homepage. "Portable Insulin Pump". www.sooil.com/product4.htm.

US 5,954,699, 09/1999, Jost et al. (withdrawn)

* cited by examiner

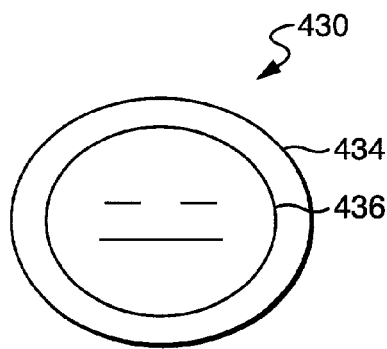
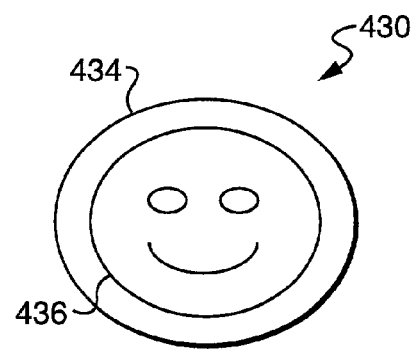
FIG. 15A       FIG. 15B
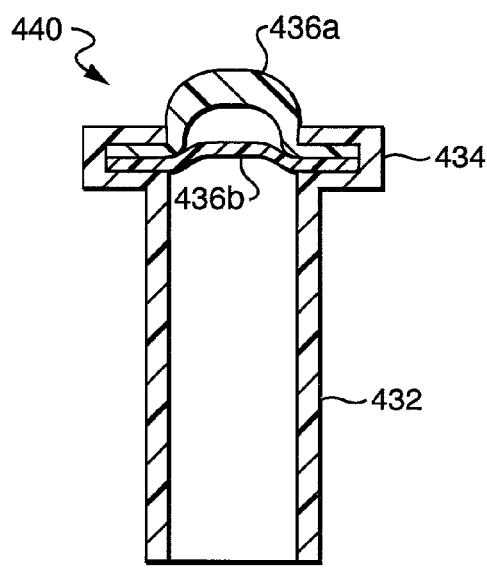
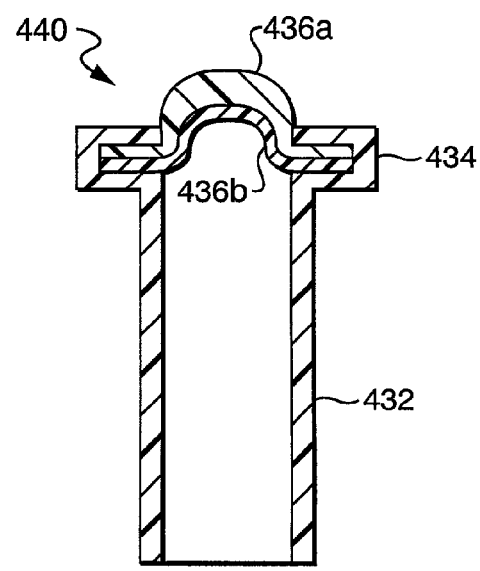
FIG. 16A       FIG. 16B

FLOW RESTRICTION SYSTEM AND METHOD FOR PATIENT INFUSION DEVICE

CROSS-REFERENCE TO RELATED APPLICATIONS

The present application is related to co-pending U.S. patent application Ser. No. 09/943,992, filed on Aug. 31, 2001, and entitled DEVICES, SYSTEMS AND METHODS FOR PATIENT INFUSION, which is assigned to the assignee of the present application and incorporated herein by reference.

FIELD OF THE INVENTION

The present invention relates generally to medical devices, systems and methods, and more particularly to small, low cost, portable infusion devices and methods that are useable to achieve precise, sophisticated, and programmable flow patterns for the delivery of therapeutic liquids such as insulin to a mammalian patient. Even more particularly, the present invention is directed to fluid flow restriction systems and methods for an infusion device. Among other benefits and features, the fluid flow restriction systems and methods of the present invention ensure adequate priming of infusion devices prior to use, and the delivery of accurate volumes of fluid from the infusion devices during their use.

BACKGROUND OF THE INVENTION

Today, there are numerous diseases and other physical ailments that are treated by various medicines including pharmaceuticals, nutritional formulas, biologically derived or active agents, hormonal and gene based material and other substances in both solid or liquid form. In the delivery of these medicines, it is often desirable to bypass the digestive system of a mammalian patient to avoid degradation of the active ingredients caused by the catalytic enzymes in the digestive tract and liver. Delivery of a medicine other than by way of the intestines is known as parenteral delivery. Parenteral delivery of various drugs in liquid form is often desired to enhance the effect of the substance being delivered, insuring that the unaltered medicine reaches its intended site at a significant concentration. Also, undesired side effects associated with other routes of delivery, such as systemic toxicity, can potentially be avoided.

Often, a medicine may only be available in a liquid form, or the liquid version may have desirable characteristics that cannot be achieved with solid or pill form. Delivery of liquid medicines may best be accomplished by infusing directly into the cardiovascular system via veins or arteries, into the subcutaneous tissue or directly into organs, tumors, cavities, bones or other site specific locations within the body.

Parenteral delivery of liquid medicines into the body is often accomplished by administering bolus injections using a needle and reservoir, or continuously by gravity driven dispensers or transdermal patch technologies. Bolus injections often imperfectly match the clinical needs of the patient, and usually require larger individual doses than are desired at the specific time they are given. Continuous delivery of medicine through gravity feed systems compromise the patient's mobility and lifestyle, and limit the therapy to simplistic flow rates and profiles. Transdermal patches have special requirements of the medicine being delivered, particularly as it relates to the molecular structure, and similar to gravity feed systems, the control of the drug administration is severely limited.

Ambulatory infusion pumps have been developed for delivering liquid medicaments to a patient. These infusion devices have the ability to offer sophisticated fluid delivery profiles accomplishing bolus requirements, continuous infusion and variable flow rate delivery. These infusion capabilities usually result in better efficacy of the drug and therapy and less toxicity to the patient's system. An example of a use of an ambulatory infusion pump is for the delivery of insulin for the treatment of diabetes mellitus. These pumps can deliver insulin on a continuous basal basis as well as a bolus basis as is disclosed in U.S. Pat. No. 4,498,843 to Schneider et al.

The ambulatory pumps often work with a reservoir to contain the liquid medicine, such as a cartridge, a syringe or an IV bag, and use electro-mechanical pumping or metering technology to deliver the medication to the patient via tubing from the infusion device to a needle that is inserted transcutaneously, or through the skin of the patient. The devices allow control and programming via electromechanical buttons or switches located on the housing of the device, and accessed by the patient or clinician. The devices include visual feedback via text or graphic screens, such as liquid crystal displays known as LCD's, and may include alert or warning lights and audio or vibration signals and alarms. The device can be worn in a harness or pocket or strapped to the body of the patient.

Currently available ambulatory infusion devices are expensive, difficult to program and prepare for infusion, and tend to be bulky, heavy and very fragile. Filling these devices can be difficult and require the patient to carry both the intended medication as well as filling accessories. The devices require specialized care, maintenance, and cleaning to assure proper functionality and safety for their intended long term use. Due to the high cost of existing devices, healthcare providers limit the patient populations approved to use the devices and therapies for which the devices can be used.

Clearly, therefore, there was a need for a programmable and adjustable infusion system that is precise and reliable and can offer clinicians and patients a small, low cost, light-weight, easy-to-use alternative for parenteral delivery of liquid medicines.

In response, the applicant of the present application provided a small, low cost, light-weight, easy-to-use device for delivering liquid medicines to a patient. The device, which is described in detail in co-pending U.S. application Ser. No. 09/943,992, filed on Aug. 31, 2001, includes an exit port, a dispenser for causing fluid from a reservoir to flow to the exit port, a local processor programmed to cause a flow of fluid to the exit port based on flow instructions from a separate, remote control device, and a wireless receiver connected to the local processor for receiving the flow instructions. To reduce the size, complexity and costs of the device, the device is provided with a housing that is free of user input components, such as a keypad, for providing flow instructions to the local processor.

Such devices for delivering liquid medicines to a patient are preferably purged of air, or "primed" prior to operation such that desired volumes of fluid are accurately delivered by the devices. What is still desired, therefore, are new and improved devices for delivering fluid to a patient. Preferably, the fluid delivery devices will be simple in design, and inexpensive and easy to manufacture, in order to further reduce the size, complexity and costs of the devices, such that the devices lend themselves to being small and disposable in nature. In addition, the fluid delivery device will preferably include a flow restriction system and method that primes the devices prior to operation.

SUMMARY OF THE INVENTION

The present invention provides a device for delivering fluid, such as insulin for example, to a patient. The device includes a flow path having an exit port assembly adapted to connect to a transcutaneous patient access tool (e.g., needle), and a reservoir connected to the exit port assembly. The device also includes a flow restriction system having an air removal filter communicating with the flow path and allowing air to exit the flow path and preventing fluid from exiting the flow path, and a flow restrictor positioned within the flow path between the air removal filter and the exit port assembly.

Among other features and advantages, the flow restriction system of the present invention allows the flow path of the fluid delivery device to be purged of air, or "primed" prior to operation, such that desired volumes of fluid can be accurately delivered by the device.

According to one aspect of the present invention, the flow restrictor of the flow restriction system comprises an outlet plug removably connected to the exit port assembly to prevent fluid from exiting the flow path through the exit port assembly. According to another aspect, the exit port assembly of the fluid delivery device includes a transcutaneous patient access tool and the outlet plug is removably connected to the access tool. According to a further aspect, the transcutaneous patient access tool comprises a needle having a distal end for insertion into a patient and the outlet plug is removably connected to the distal end of the needle.

According to another aspect of the present invention, the air removal filter of the flow restriction system comprises at least a portion of the outlet plug allowing air to exit the flow path through the exit port assembly. According to an additional aspect, the air removal filter of the outlet plug comprises one of PTFE and polyethylene. According to a further aspect, the air removal filter of the outlet plug is provided with predetermined physical properties (e.g., pore size and/or thickness) such that the filter expands upon the flow path being substantially primed. According to yet another aspect, the air bubble removal filter of the outlet plug comprises needle septum material.

According to an additional aspect of the present invention, the flow restriction system further comprises a second air removal filter positioned between the fill port and the reservoir. According to another aspect, the flow restriction system further comprises a second flow restrictor positioned between the second air removal filter and the reservoir.

According to a further aspect of the present invention, the flow restriction system also includes a sensor assembly monitoring fluid flow conditions within the flow path. According to one aspect, the sensor assembly includes a resilient diaphragm having opposing first and second surfaces, with the first surface of the diaphragm positioned against the flow path, a chamber wall positioned adjacent the second surface of the diaphragm and defining a sensor chamber adjacent the second surface of the diaphragm, and at least one sensor arranged to provide a signal when the second surface of the diaphragm expands into the chamber. According to an additional aspect, the sensor assembly is adapted to provide a signal to the processor when the flow path is primed.

The present invention also provides a method for restricting fluid flow in a flow path of a fluid delivery device having an exit port assembly adapted to connect to a transcutaneous patient access tool. The method includes preventing fluid from exiting the flow path, allowing air to exit the flow path at an air removal point within the flow path, and restricting fluid flow through the flow path between the air removal point and the exit port assembly.

These aspects of the invention together with additional features and advantages thereof may best be understood by reference to the following detailed descriptions and examples taken in connection with the accompanying illustrated drawings.

BRIEF DESCRIPTION OF THE DRAWINGS

FIG. 6 is a graph illustrating an exemplary embodiment of a method of restricting flow according to the present invention as carried out by the flow sensor assembly of the fluid delivery device of FIGS. 5 and 5a;

FIG. 9 is an enlarged sectional view of an exemplary embodiment of an outlet plug constructed in accordance with the present invention for use as part of the flow restriction system of FIG. 4a;

FIGS. 15a and 15b are top plan views of another exemplary embodiment of an outlet plug constructed in accordance with the present invention, respectively showing an air bubble filter of the outlet plug before and after expansion;

FIGS. 16a and 16b are side sectional views of another exemplary embodiment of an outlet plug constructed in accordance with the present invention, respectively showing an air bubble filter of the outlet plug before and after expansion;

FIG. 20b is a side elevation view, partially cut-away, showing the outlet plug removed from the fluid delivery device of FIG. 20a;

Like reference characters designate identical or corresponding components and units throughout the several views.

DETAILED DESCRIPTION OF THE PREFERRED EMBODIMENTS

Figure 2:
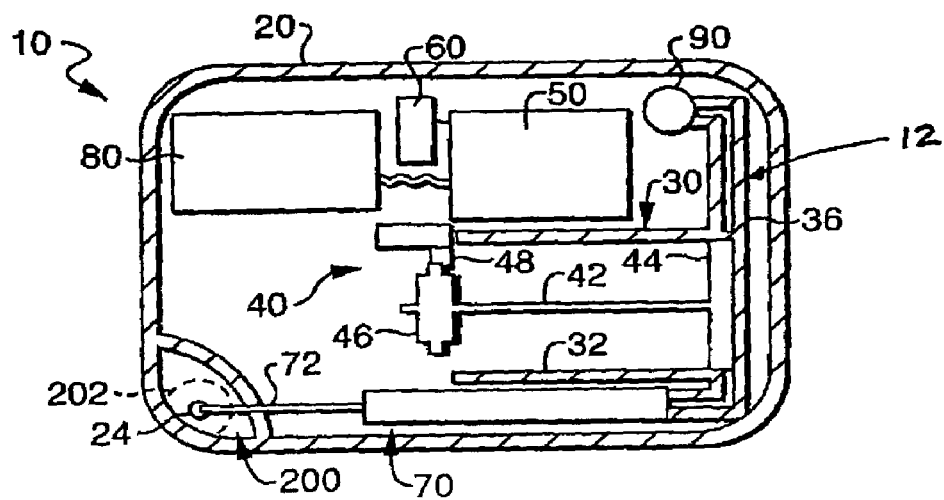
FIG. 2 is an enlarged top sectional view of the fluid delivery device of FIG. 1.

Referring first to FIG. 2, there is illustrated a fluid delivery device 10 including a flow restriction system 200 constructed in accordance with the present invention. The flow restriction system 200 operates to substantially prime (i.e., purge of air) a flow path 12 of the fluid delivery device 10 prior to operation of the device 10, to ensure that a desired volume of fluid is accurately delivered by the device 10 during operation.

Figure 3:
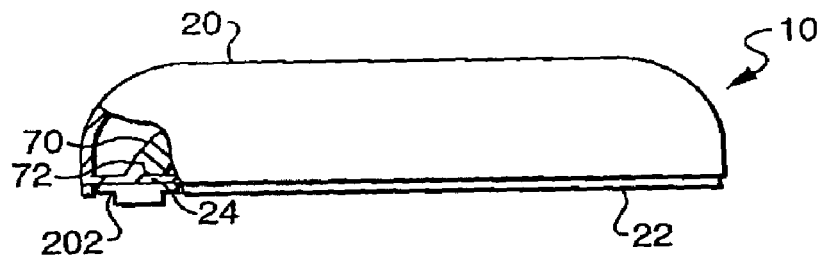
FIG. 3 is an enlarged side elevation view, partially cut-away, of the fluid delivery device of FIG. 1.
Figure 4:
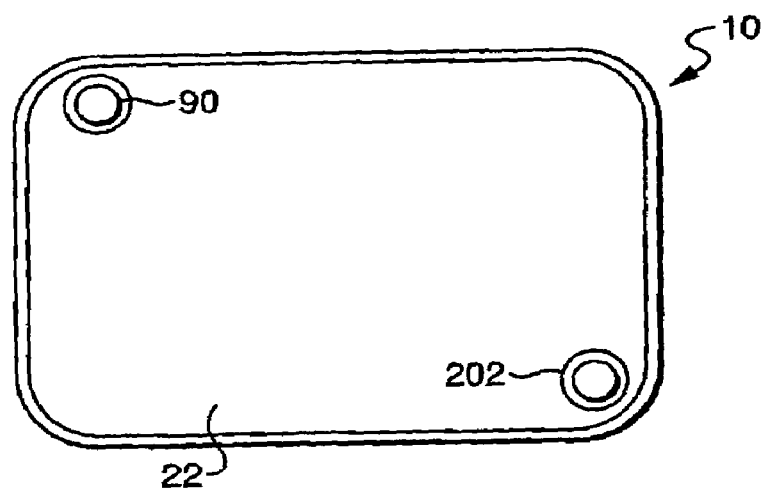
FIG. 4 is an enlarged bottom plan view of the fluid delivery device of FIG. 1.

The fluid delivery device 10 of FIG. 2, and which is also shown in FIGS. 3 and 4, can be used for the delivery of fluids to a person or animal. The types of liquids that can be delivered by the fluid delivery device 10 include, but are not limited to, insulin, antibiotics, nutritional fluids, total parenteral nutrition or TPN, analgesics, morphine, hormones or hormonal drugs, gene therapy drugs, anticoagulants, analgesics, cardiovascular medications, AZT or chemotherapeutics. The types of medical conditions that the fluid delivery device 10 might be used to treat include, but are not limited to, diabetes, cardiovascular disease, pain, chronic pain, cancer, AIDS, neurological diseases, Alzheimer's Disease, ALS, Hepatitis, Parkinson's Disease or spasticity. In addition, it should be understood that the flow restriction assembly 200 according to the present invention can be used with fluid delivery devices other than those used for the delivery of fluids to persons or animals.

The flow path 12 of the fluid delivery device 10, as shown in FIG. 2, generally includes a reservoir 30 for receiving and holding the fluid to be delivered by the device 10, an exit port assembly 70 connected to the reservoir, and a fill port connected to the reservoir. The fluid delivery device 10 also includes a dispenser 40 for causing fluid from the reservoir 30 to flow to the exit port assembly 70.

The volume of the reservoir 30 is chosen to best suit the therapeutic application of the fluid delivery device 10 impacted by such factors as available concentrations of medicinal fluids to be delivered, acceptable times between refills or disposal of the fluid delivery device 10, size constraints and other factors. The reservoir 30 may be prefilled by the device manufacturer or a cooperating drug manufacturer, or may include external filling means, such as a fill port 90 having needle insertion septum or a Luer connector, for example. In addition, the device 10 can be provided with a removable reservoir.

The exit port assembly 70 can include elements to penetrate the skin of the patient, such that the entire volume of the flow path 12 of the fluid delivery device 10 is predetermined. For example, in the exemplary embodiment shown in FIG. 3, a needle-connection tubing terminating in a skin penetrating cannula 72 is provided as an integral part of the exit port assembly 70. The exit port assembly 70 can further be provided with injection means, such as a spring-biased mechanism driven by a shaped memory element, to inject the skin penetrating cannula 72 into a patient when the fluid delivery device 10 is correctly positioned on the patient. For example, if the cannula is a flexible tube, a rigid penetrator within the lumen of the tube can be driven through the skin by the injection means and then withdrawn, leaving the soft cannula in place in the subcutaneous tissue of the patient or other internal site.

Examples of injection means for the exit port assembly are shown in co-pending U.S. patent application Ser. No. 10/037,902, filed on Nov. 9, 2001, and entitled TRANSCUTANEOUS DELIVERY MEANS, and U.S. patent application Ser. No. 10/128,206, filed on Apr. 23, 2002, and entitled TRANSCUTANEOUS FLUID DELIVERY SYSTEM, both of which are assigned to the assignee of the present application and incorporated herein by reference.

Alternatively, the injection means may be removable soon after transcutaneous penetration. In addition, the exit port assembly 70 can simply be adapted to connect with a Luer connector for example, to a separate, standard infusion device that includes a skin penetrating cannula. The exit port assembly 70 can alternatively be adapted to connect through tubing to another medical device.

It should be understood that, as used herein, the term "flow path" 12 is meant to include all portions of the fluid delivery device 10 that contain therapeutic fluid for delivery to a patient, e.g., all portions between the fill port 90 of the reservoir 30 to the tip of the needle 72 of the exit port assembly 72.

The fluid delivery device 10 also includes a processor or electronic microcontroller (hereinafter referred to as the "local" processor) 50 connected to the dispenser 40. The local processor 50 is programmed to cause a flow of fluid to the exit port assembly 70 based on flow instructions from a separate, remote control device 100, an example of which is shown in FIG. 1.

Figure 1:
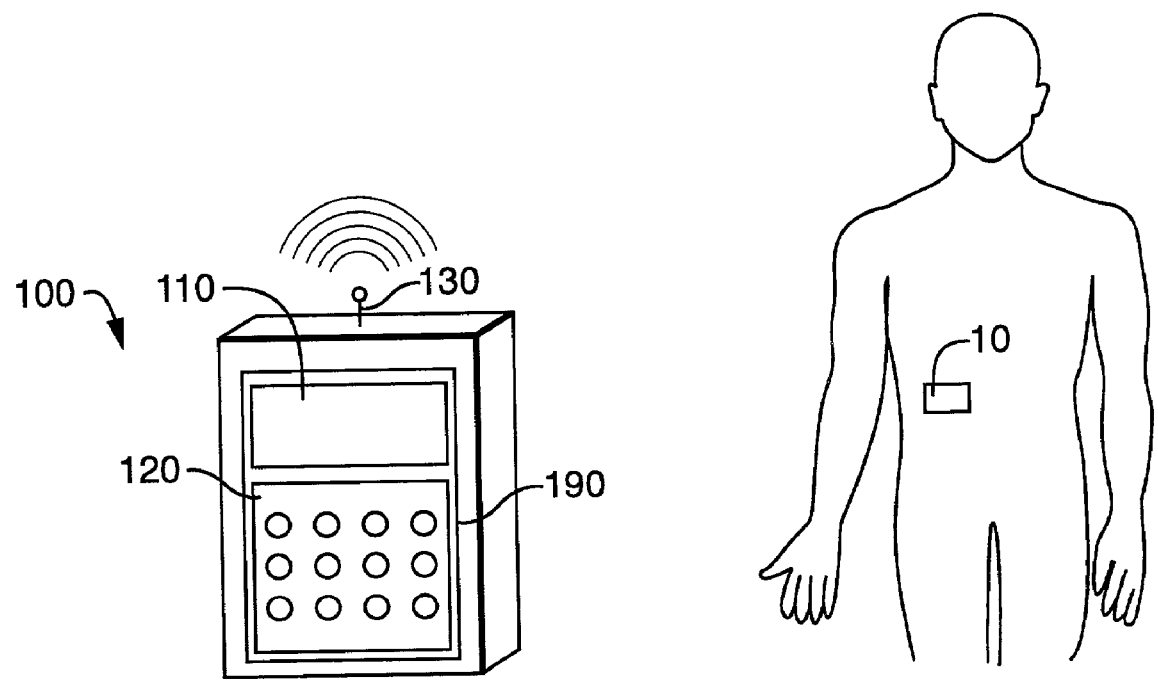
FIG. 1 is a perspective view of a first exemplary embodiment of a fluid delivery device constructed in accordance with the present invention shown secured on a patient, and a remote control device for use with the fluid delivery device (the remote control device being enlarged with respect to the patient and the fluid delivery device for purposes of illustration)

Referring also to FIG. 1, the fluid delivery device 10 further includes a wireless receiver 60 connected to the local processor 50 for receiving flow instructions from a separate, remote control device 100 and delivering the flow instructions to the local processor 50. The device 10 also includes a housing 20 containing the exit port assembly 70, the reservoir 30, the dispenser 40, the local processor 50, and the wireless receiver 60.

As shown best in FIGS. 3 and 4, the housing 20 of the fluid delivery device 10 is free of user input components for providing flow instructions to the local processor 50, such as electromechanical switches or buttons on an outer surface of the housing 20, or interfaces otherwise accessible to a user to adjust the programmed flow rate through the local processor 50. The lack of user input components allows the size, complexity and costs of the device 10 to be substantially reduced so that the device 10 lends itself to being small and disposable in nature. Examples of such devices are disclosed in co-pending U.S. patent application Ser. No. 09/943,992, filed on Aug. 31, 2001, and entitled DEVICES, SYSTEMS AND METHODS FOR PATIENT INFUSION, which is assigned to the assignee of the present application and has previously been incorporated herein by reference.

In order to program, adjust the programming of, or otherwise communicate user inputs to the local processor 50, the fluid delivery device 10 includes the wireless communication element, or receiver 60 for receiving the user inputs from the separate, remote control device 100 of FIG. 1. Signals can be sent via a communication element (not shown) of the remote control device 100, which can include or be connected to an antenna 130, shown in FIG. 1 as being external to the device 100.

The remote control device 100 has user input components, including an array of electromechanical switches, such as the membrane keypad 120 shown. The control device 100 also includes user output components, including a visual display, such as a liquid crystal display (LCD) 110. Alternatively, the control device can be provided with a touch screen for both user input and output. Although not shown in FIG. 1, the remote control device 100 has its own processor (hereinafter referred to as the "remote" processor) connected to the membrane keypad 120 and the LCD 110. The remote processor receives the user inputs from the membrane keypad 120 and provides "flow" instructions for transmission to the fluid delivery device 10, and provides information to the LCD 110. Since the remote control device 100 also includes a visual display 110, the fluid delivery device 10 can be void of an information screen, further reducing the size, complexity and costs of the device 10.

The communication element 60 of the device 10 preferably receives electronic communication from the remote control device 100 using radio frequency or other wireless communication standards and protocols. In a preferred embodiment, the communication element 60 is a two-way communication element, including a receiver and a transmitter, for allowing the fluid delivery device 10 to send information back to the remote control device 100. In such an embodiment, the remote control device 100 also includes an integral communication element comprising a receiver and a transmitter, for allowing the remote control device 100 to receive the information sent by the fluid delivery device 10.

The local processor 50 of the device 10 contains all the computer programs and electronic circuitry needed to allow a user to program the desired flow patterns and adjust the program as necessary. Such circuitry can include one or more microprocessors, digital and analog integrated circuits, resistors, capacitors, transistors and other semiconductors and other electronic components known to those skilled in the art. The local processor 50 also includes programming, electronic circuitry and memory to properly activate the dispenser 40 at the needed time intervals.

In the exemplary embodiment of FIG. 2, the device 10 includes a power supply 80, such as a battery or capacitor, for supplying power to the local processor 50. The power supply 80 is preferably integrated into the fluid delivery device 10, but can be provided as replaceable, e.g., a replaceable battery.

Although not shown, the device 10 can include sensors or transducers such as a reservoir volume transducer or a reservoir pressure transducer, for transmitting information to the local processor 50 to indicate how and when to activate the dispenser 40, or to indicate other parameters determining flow, blockage in flow path, contact sensors, rotary motion or other motion indicators, as well as conditions such as the reservoir 30 being empty or leaking, or the dispensing of too much or too little fluid from the reservoir, etc.

As shown in FIGS. 3 and 4, the device 10 can also be provided with an adhesive layer 22 on the outer surface of the housing 20 for securing the device 10 directly to the skin of a patient, as illustrated in FIG. 1. The adhesive layer 22 is provided on an external "bottom" surface of the housing 20. The adhesive layer is also preferably provided in a continuous ring encircling the port 24 of the exit port assembly 70 in order to provide a protective seal around the penetrated skin to prevent the penetrated skin from becoming dirty when the cannula 72 of the exit port assembly 70 extends through the skin. It is preferably that the fill port 90 extend through the bottom surface of the housing 20 and be surrounded by the adhesive layer 22 to discourage and prevent filling and re-filling of the fluid delivery device 10 when the device is attached to a patient's skin. The housing 20 can be made from flexible material, or can be provided with flexible hinged sections that allow the fluid delivery device 10 to flex during patient movement to prevent detachment and aid in patient comfort.

Figure 5:
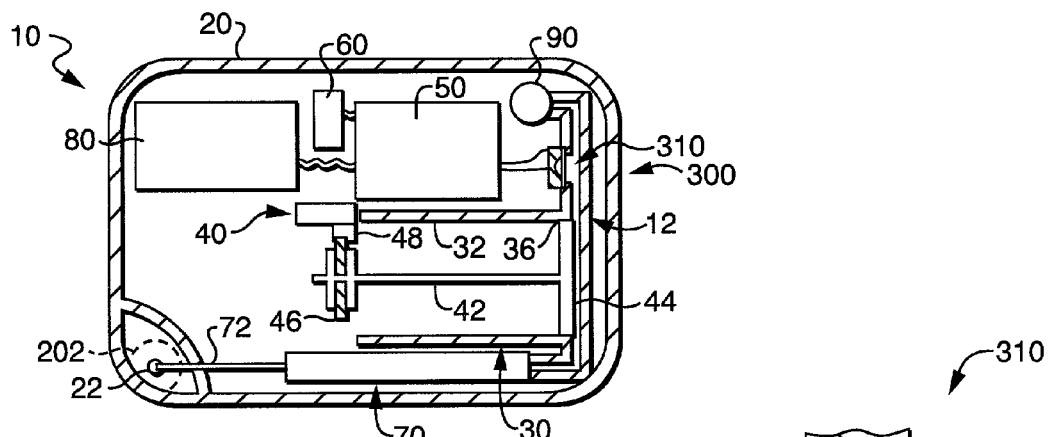
FIG. 5 is an enlarged top sectional view of another exemplary embodiment of a fluid delivery device constructed in accordance with the present invention.

In the exemplary embodiment of FIGS. 4 and 5, the device 10 is provided with a non-pressurized reservoir 30, and the dispenser 40 is adapted to control flow from the reservoir 30 by driving or pumping the fluid from the reservoir to the exit port assembly.

Examples of such "driving or pumping" dispensers are shown in co-pending U.S. patent application Ser. No. 09/955,623, filed on Sep. 19, 2001, and entitled PLUNGER FOR PATIENT INFUSION DEVICE, which is assigned to the assignee of the present application and incorporated herein by reference. Other examples of dispensers are shown in co-pending U.S. patent application Ser. No. 10/128,205, filed on Apr. 23, 2002, and entitled DISPENSER FOR PATIENT INFUSION DEVICE, which is assigned to the assignee of the present application and incorporated herein by reference, and co-pending U.S. patent application Ser. No. 10/128,203, filed on Apr. 23, 2002, and entitled DISPENSER FOR PATIENT INFUSION DEVICE, which is assigned to the assignee of the present application and incorporated herein by reference. Further examples of dispensers are shown in co-pending U.S. patent application serial number [pending], filed on Jun. 9, 2002, and entitled PLUNGER FOR PATIENT INFUSION DEVICE, which is assigned to the assignee of the present application and incorporated herein by reference, and in co-pending U.S. patent application serial number [pending], filed on Jun. 9, 2002, and entitled PLUNGER FOR PATIENT INFUSION DEVICE, which is also assigned to the assignee of the present application and incorporated herein by reference.

In the embodiment shown in FIGS. 4 and 5, the reservoir 30 includes a side wall 32 extending towards an outlet 36 connected to the exit port assembly 70. A threaded lead screw 42 is received in the reservoir 30 and extends towards the outlet 36 of the reservoir 30 generally parallel with the side wall 32 of the reservoir, and a plunger 44 is secured to an end of the lead screw 42. The lead screw 42, the plunger 44 and the reservoir 30 are adapted such that a fluid-tight seal is formed between the plunger and the lead screw and a fluid-tight seal is formed between the plunger and the side wall 32 of the reservoir, so that movement of the plunger towards the outlet 36 of the reservoir 30 forces fluid through the outlet 36 to the exit port assembly 70.

The dispenser 40 causes fluid flow by causing linear movement of the lead screw 42 and the plunger 44 towards the outlet 36 of the reservoir 30. Although not shown, the dispenser 40 can include an elongated shape memory element connected to the local processor 50 and having a changeable length decreasing from an uncharged length to a charged length when at least one charge is applied to the shape memory element. The shape memory element is operatively connected to the plunger 44 such that the changeable length of the shape memory element causes the plunger 44 to move along the side wall 32 of the reservoir 30.

In the embodiment shown, the dispenser 40 includes a rotatable gear 46 linearly fixed with respect to the reservoir 30. The gear 46 is coaxially mounted with respect to the lead screw 42, and is threadedly engaged with the lead screw 42, such that rotation of the gear 46 causes linear movement of the lead screw 42. In particular, the lead screw 42 and the gear 46 are adapted such that rotation of the gear 46 in a first direction causes linear movement of the lead screw 42 and the plunger 44 towards the outlet 36 of the reservoir 30.

The dispenser 40 further includes a finger 48 for engaging radially extending teeth of the gear 46, wherein the finger 48 and the gear 46 are adapted such that linear movement of the finger 48 in a first direction adjacent the gear 46 causes rotation of the gear while linear movement of the finger 48 in a second direction adjacent the gear 46 causes no rotation of the gear. Although not shown, the elongated shape memory element is connected to the finger 48 such that the changeable length of the shape memory element decreasing from an uncharged length to a charged length causes linear movement of the finger 48 in one of the first and the second directions. The dispenser 40 can also include an actuation element, such as a compression spring, connected to the finger 48 for causing linear movement of the finger in the first direction. Examples of such dispensers are shown in co-pending U.S. patent application Ser. No. 10/128,205, filed on Apr. 23, 2002, which has already been incorporated herein by reference.

Although not shown, the gear 46 can be further configured to be released from the lead screw 42 to allow the lead screw 42 and the plunger 44 to be linearly moved away from the outlet 36 of the reservoir 30 during filling of the reservoir. An example of such a releasable gear is also shown in co-pending U.S. patent application Ser. No. 10/128,205, filed on Apr. 23, 2002, which has already been incorporated herein by reference.

It should be understood, however, that other types of dispensers can also be used with a device incorporating a flow restriction assembly 200 of the present invention. For example, the device can be provided with a pressurized reservoir and a dispenser that does not create a driving or pumping force, but rather acts as a metering device, allowing pulses of fluid to pass from the pressurized reservoir, through the dispenser, to the exit port assembly 70. Examples of such "metering" dispensers are shown in co-pending U.S. patent application Ser. No. 09/977,434, filed Oct. 12, 2001, and entitled LAMINATED PATIENT INFUSION DEVICE, which is assigned to the assignee of the present application and incorporated herein by reference. In any event, the dispenser is controlled by the local processor 50, which includes electronic programming, controls, and circuitry to allow sophisticated fluid delivery programming and control of the dispenser.

Referring now to FIGS. 2 through 4, an exemplary embodiment of the flow restriction system 200 of the present invention is shown. The flow restriction system 200 generally includes an air removal filter communicating with the flow path 12 and allowing air to exit the flow path 12 and preventing fluid from exiting the flow path 12, and a flow restrictor positioned within the flow path 12 between the air removal filter and the exit port assembly 70 (i.e., downstream of the filter). Among other features and advantages, the flow restriction system 200 of the present invention allows the flow path 12 of the fluid delivery device 10 to be purged of air, or "primed" prior to operation, such that desired volumes of fluid can be accurately delivered by the device 10. In particular, the air removal filter of the flow restriction system 200 removes air from the flow path 12, while the flow restrictor of the flow restriction system 200 elevates pressure within the flow path 12 to ensure that substantially all air within the flow path 12 is forced out of the air removal filter.

In the exemplary embodiment of FIGS. 2 through 4, the flow restrictor and the air removal filter of the flow restriction system 200 are combined in a single outlet plug 202 fitted to the port 24 of the exit port assembly 70. The outlet plug 202 is unitarily formed of a material that allows the passage of air but prevents the passage of fluid, such as an ultrahigh molecular weight polyethylene in sinstered porous form, a porous ceramic, a hydrophobic gel, a woven or non-woven polytetrafluoroethylene (PTFE) such as Teflon®, or woven fabric material having very small openings (e.g., 0.02 microns) such as Gortex®.

In the exemplary embodiment of FIGS. 2 through 4, the flow restrictor and the air removal filter of the flow restriction system 200 are positioned between the reservoir 30 and the outlet port assembly 70. However, the flow restrictor and the air removal filter of the flow restriction system 200 could be positioned before the reservoir 30, as long as the flow restrictor is positioned downstream of the air removal filter.

The removable outlet plug 202 prevents fluid leakage from the flow path 12 prior to use, e.g., during storage and during priming when filled by a user. The outlet plug 202 may also maintain the cannula 72 of the exit port assembly 70 in a sterile state prior to use. The outlet plug 202 is removed by a user prior to attaching the fluid delivery device 10 to a patient's skin surface. In the embodiment shown, the cannula 72 of the exit port assembly 70 is extendable through the port 22 in the housing 20 of the fluid delivery device 10 to be inserted into the skin of a patient. The outlet plug 202 is removably secured to the outer surface of the housing 20 over the port 22, such that the outlet plug 202 prevents fluid from exiting the flow path 12.

FIG. 5 shows another exemplary embodiment of a fluid delivery device 10 including a flow restriction system 300 constructed in accordance with the present invention. The system 300 of FIG. 5 is similar to the system 200 of FIGS. 2 through 4 such that similar elements have the same reference numeral. The flow restriction system 300 of FIG. 5, however, further includes a flow sensor assembly 310 that provides an indication of fluid pressure within the flow path 12, so that conditions within the flow path 12 can be determined during a filling process. In particular, the flow sensor assembly 310 can be used to provide an indication of when the flow path 12 is full and when the flow path 12 becomes primed.

Figure 5A:
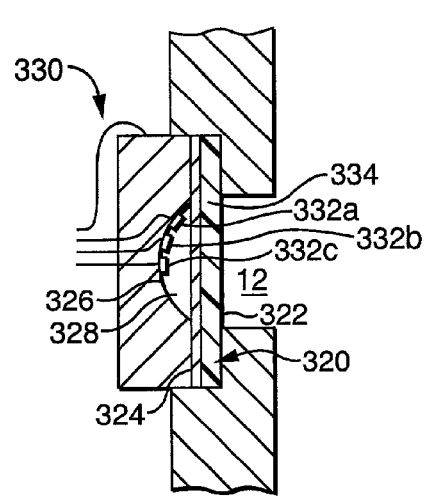
FIG. 5a is a further enlarged sectional view of an exemplary embodiment of a flow sensor assembly of the fluid delivery device of FIG. 5.

In the exemplary embodiment, as also shown in FIG. 5a, the flow sensor assembly 310 comprises a resilient diaphragm 320 having opposing first and second surfaces 322, 324, with the first surface 322 positioned against the flow path 12 of the device 10, and a chamber wall 326 positioned adjacent the second surface 324 of the diaphragm. The diaphragm 320 is made from a suitably expandable yet resilient material, such as rubber or a synthetic rubber. The chamber wall 326 is adapted such that an enclosed chamber 328 is defined between the chamber wall 326 and the second surface 324 of the diaphragm 320. Preferably, the chamber 328 is provided with a predetermined volume. Although not shown, the chamber 328 can also be provided with a relief port for allowing air to escape the chamber upon expansion of the diaphragm 320.

The diaphragm 320 and the chamber 328 are arranged and adapted such that the amount of expansion and the duration of the expansion of the diaphragm into the chamber can be used to determine when the flow path 12 becomes substantially primed upon being filled through the fill port 90. The sensor assembly 310 also includes at least one sensor 330 arranged to provide a signal when the second surface 324 of the diaphragm 320 expands into the chamber 328 in response to at least one predetermined fluid flow condition occurring in the flow path 12. For example, the sensor 330 can be arranged to determine when the second surface 324 of the diaphragm 320 expands fully into the chamber 328 and contacts the chamber wall 326.

The sensor 330 can comprise any device for determining and providing an indication of the position of the diaphragm 320 in the chamber 328. For example, the sensor can comprise one of a contact or pressure switch, a magnetic Hall effect sensor, a strain gage, and a density gage. In the embodiment of FIG. 5a, the sensor comprises three open circuits 330a, 330b, 330c, which each have their own primary leads 332a, 332b, 332c and share a secondary lead 334. The secondary lead 334 is positioned on the second surface 324 of the diaphragm 320, while the primary leads 332a, 332b, 332c are positioned on the chamber wall 326 at different points from the diaphragm 320. During expansion of the diaphragm 320 into the chamber 328, the secondary lead 334 of the diaphragm 320 eventually contacts each of primary leads 332a, 332b, 332c, and successively closes the circuits 330a, 330b, 330c.

In the embodiment 300 of the invention illustrated in FIGS. 2, the processor 50 of the fluid delivery device 10 also acts as the processor for the sensor assembly 300 and is connected to the open circuits 330a, 330b, 330c. During expansion of the diaphragm 320 into the chamber 328, the circuits 330a, 330b, 330c are successively closed to provide "signals" to the processor 50. Alternatively, the sensor assembly 300 can be provided with its own, separate processor programmed to operate in accordance with the present invention. In addition, the sensors 330a, 330b, 330c can simply be connected to an alarm(s), such as a light emitting diode or an electronic sound maker, and which is activated upon the circuits 330a, 330b, 330c being closed. In this manner, a user can simply receive a visual or an audible alarm signal upon full expansion of the diaphragm 320 into the chamber 328 to close the circuits 330a, 330b, 330c.

Figure 6:
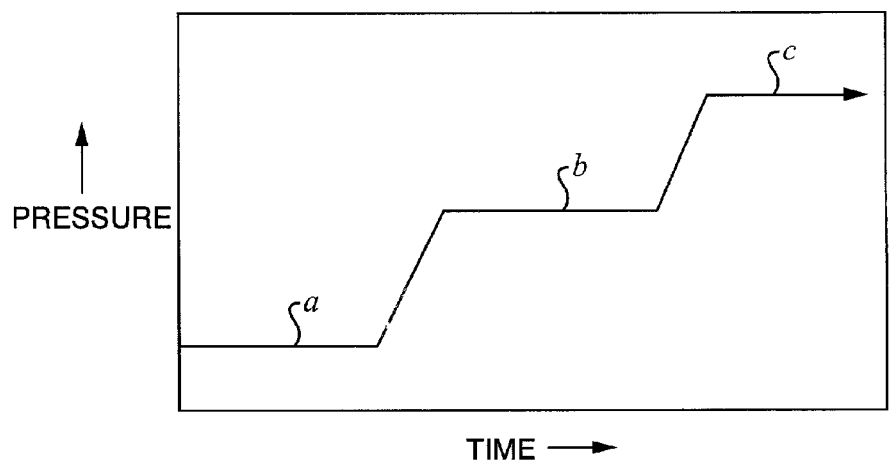

FIG. 6 illustrates an exemplary embodiment of a method of determining when the flow path 12 is primed in accordance with the present invention and as carried out by the processor 50. FIG. 6 is a graph of pressure versus time illustrating pressure within the flow path while the flow path is being filled by a user. The pressure level "a" illustrated in the graph is produced upon the second surface 324 of the diaphragm 320 expanding partly into the chamber 328 and closing the first sensor circuit 330a, shown in FIG. 5a. Upon receiving signal "a" from the first sensor circuit 330a, the processor 50 is programmed to send a signal to the remote control device 100 indicating that the flow delivery device 10 is being filled. Although not shown, the remote control device 100 can include an alarm, such as an audible or visual alarm, that the remote processor of the remote control device 100 activates upon receiving the signal from the local processor 50. In addition, the fluid delivery device 10 itself can be provided with an alarm, such as a light emitting diode or electronic buzzer, connected to the local processor 50 for activation at least initially when the flow path is being filled by a user.

The pressure level "b" illustrated in the graph is produced upon the second surface 324 of the diaphragm 320 further expanding into the chamber 328 and closing the second sensor circuit 330b. Upon receiving signal "b" from the second sensor circuit 330b, the processor 50 is programmed to send a signal to the remote control device 100 indicating that the plunger 44 of the flow delivery device 10 has been fully moved rearward within the reservoir 30 and away from the outlet 36 of the reservoir. Although not shown, the remote control device 100 can include another alarm, such as an audible or visual alarm, that the remote processor of the remote control device 100 activates upon receiving the signal from the local processor 50. In addition, the fluid delivery device 10 itself can be provided with an alarm, such as a light emitting diode or electronic buzzer, connected to the local processor 50 for activation when the plunger 44 has been fully moved rearward within the reservoir 30.

The pressure level "c" illustrated in the graph is produced upon the third surface 324 of the diaphragm 320 fully expanding into the chamber 328 and closing the third sensor circuit 330c. Upon receiving signal "c" from the third sensor circuit 330c, the processor 50 is programmed to send a signal to the remote control device 100 indicating that the flow path 12 is filled and primed. Although not shown, the remote control device 100 can include another alarm, such as an audible or visual alarm, that the remote processor of the remote control device 100 activates upon receiving the signal from the local processor 50. In addition, the fluid delivery device 10 itself can be provided with an alarm, such as a light emitting diode or electronic buzzer, connected to the local processor 50 for activation when the flow path is primed.

The preferred volume of the chamber 328 should take into account the compliance of the entire flow path 12 of the device 10. At relative filling pressures, the flow path 12 may expand, thereby artificially adding to the volume of the sensor chamber 328. Any such artificially expanded volume must be taken into account in monitoring the signals received from the sensor. Preferably, the flow path 12 is designed to have minimal compliance at both normal operating pressures and abnormal operating pressures. If minimal compliance of the flow path 12 is not possible, however, the computer algorithm of the processor can be programmed to take the known compliance of the flow path 12 into account when determining flow conditions based upon signals received from the sensor assembly 310.

Preferably, the flow path 12 as well as the sensor assembly 310 is constructed from laminated layers of suitably strong and rigid material such as plastic or stainless steel, and can be secured together in a suitable manner, such as with adhesives or by welding. The laminated construction provides many benefits including, but not limited to, simplifying the design and manufacturing of the flow path 12 and the sensor assembly 310, and further reducing the size, complexity and costs of the fluid delivery device 10, so that the device lends itself to being small and disposable in nature.

In alternative embodiments, the diaphragm 320 of the flow sensor assembly 310 can be provided as other than a flat layer of resiliently expandable material. The diaphragm can include any structure that provides a fluid-tight barrier between the flow path 12 and the sensor chamber 328, and that moves into the chamber upon an increase in pressure in the flow path 12. For example, the diaphragm may be provided as a piston biased away from the chamber wall with a spring. Many alternative embodiments of the diaphragm are possible while remaining within the scope of the present invention. Examples of flow sensor assemblies are shown in copending U.S. patent application Ser. No. 10/087,507, filed on Mar. 1, 2002, and entitled FLOW CONDITION SENSOR ASSEMBLY FOR PATIENT INFUSION DEVICE, which is assigned to the assignee of the present application and incorporated herein by reference. Moreover, in alternative embodiments of the present invention, the flow sensor assembly can be provided in the form of a simple pressure sensor for determining when the flow path 12 reaches a primed pressure.

Figure 7:
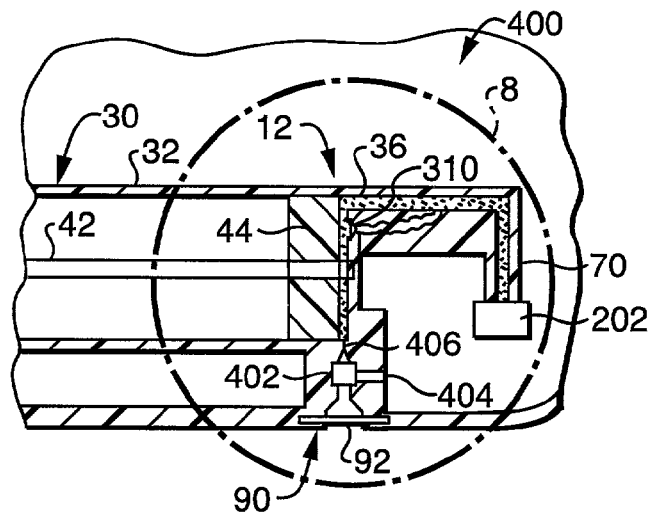
FIG. 7 is a sectional view of another exemplary embodiment of a flow restriction system constructed in accordance with the present invention.
Figure 8:
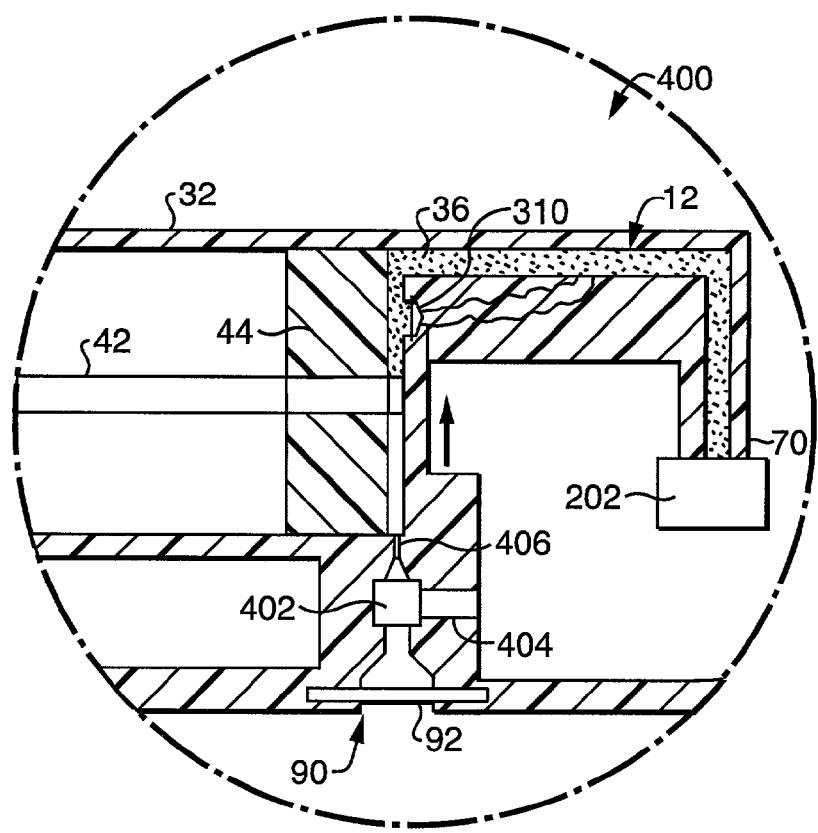
FIG. 8 is an enlarged sectional view of a portion of the exemplary embodiment of a flow restriction system contained in circle 8 of FIG. 7.

FIGS. 7 and 8 show another exemplary embodiment of a flow restriction system constructed in accordance with the present invention. The system 400 of FIGS. 7 and 8 is similar to the system 300 of FIG. 5 such that similar elements have the same reference numeral. The flow restriction system 400 of FIGS. 7 and 8, however, further includes a second air removal filter 402 positioned between the fill port 90 and the reservoir 30. The fill port 90 can include a resealing needle insertion septum 92 for receiving a needle and which can be constructed of a resealing elastomer such as silicone that allows a needle to puncture the septum to add fluid to the reservoir 30 through the fill port 90, yet reseals after the needle is withdrawn. Alternatively, the fill port 90 can include a Luer or other connector.

The second air removal filter is a flat sheet positioned in the flow path 12 just after the fill port 90, and can be comprised of any material for filtering air from fluid, such as an ultrahigh molecular weight polyethylene in sintered porous form, porous ceramic, hydrophobic gel, a woven or non-woven polytetrafluoroethylene (PTFE) such as Teflon@, woven fabric material having very small openings (e.g., 0.02 microns) such as Goretex®, or hydrophilic material that swells with fluid pressure. The flow path 12 includes an air escape port 404 extending from the filter 402 for allowing filtered air to be directed out of the flow path 12.

In the exemplary embodiment of FIGS. 7 and 8, the flow restriction system 400 also includes a second flow restrictor 406 positioned between the second air removal filter 402 and the reservoir 30. The second flow restrictor comprises a narrowed portion 406 of the flow path 12 and elevates pressure within the flow path 12 to ensure that the second air removal filter 402 operates efficiently in removing air from fluid (e.g., insulin) injected into the flow path 12 through the fill port 90.

In the exemplary embodiment of FIGS. 7 and 8, the sensor assembly 310 is positioned at the end of the reservoir 30. Positioning the sensor assembly 310 at the end of the reservoir 30 can simplify the manufacturing process of the sensor assembly 310 and the fluid delivery device 10 and can reduce the number of parts to be assembled.

Figure 11:
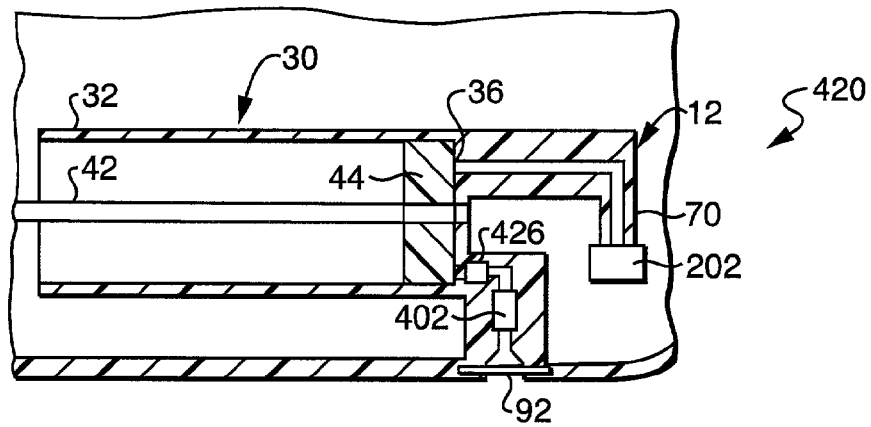
FIG. 11 is a sectional view of an additional exemplary embodiment of a flow restriction system constructed in accordance with the present invention.

FIG. 11 shows another exemplary embodiment of a flow restriction system 420 constructed in accordance with the present invention. The system 420 of FIG. 11 is similar to the system 400 of FIGS. 7 and 8 such that similar elements have the same reference numeral. The flow restriction system 420 of FIG. 11, however, includes a second flow restrictor comprising a porous plug 426 fitted in the flow path 12 to elevate pressure within the flow path 12 and ensure that the second air removal filter 402 operates efficiently in removing air from fluid (e.g., insulin) injected into the flow path through the fill port 90.

Figure 9:
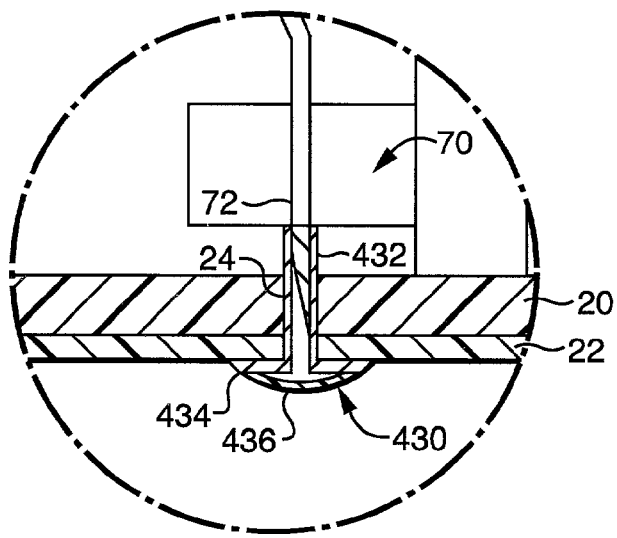
Figure 10A:
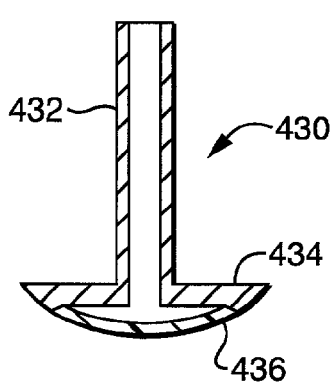
FIG. 10a is a further enlarged sectional view of the outlet plug of FIG. 9.
Figure 10B:
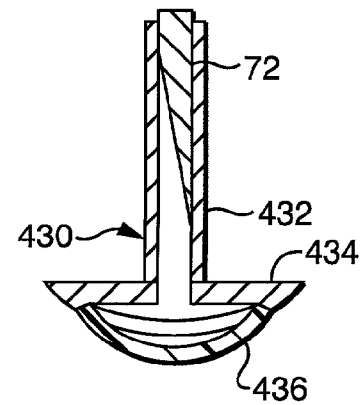
FIG. 10b is an enlarged sectional view of the outlet plug of FIG. 9 shown received on an exit port cannula of the fluid delivery device, after the device has been filled with fluid and purged of air.

FIG. 9 shows an exemplary embodiment of an outlet plug 430 constructed in accordance with the present invention. The outlet plug 430 is adapted to be received on a needle 72 of an outlet port assembly 70 of a fluid delivery device. The outlet plug 430 includes a sleeve 432 having a first end removably received in a substantially fluid-tight manner on the distal end of the needle 72, and a cap 434 connected to a second end of the sleeve 432. In the embodiment shown, the sleeve 432 and the cap 434 of the outlet plug 430 are unitarily formed from a resiliently flexible material, such as a synthetic rubber. An air removal filter 436 is seated in the cap 434 of the outlet plug 430 and prevents fluid from passing out of the needle 72 and allows air to pass out of the needle 72. As shown in FIGS. 10a and 10b, the air removal filter 436 is provided with predetermined physical properties, such as material pore size and/or thickness, such that the filter 436 expands upon the flow path being substantially primed.

The air removal filter 436 can additionally be provided with specific visual indicia for indicating when the flow path is substantially primed. For example, FIGS. 15a and 15b, show an exemplary embodiment of the outlet plug 430 wherein the visual indicia comprises a drawing on the filter 436 that changes shape upon the filter expanding. For example, the drawing can comprise two eyes and a mouth that appear as a "sad face" when the filter 436 is not expanded, as shown in FIG. 15a, and that become a "happy face" upon the filter 436 expanding when the flow path is primed, as shown in FIG. 15b. Other drawings can alternatively be used to provide an effective indication of filter 436 expansion and the flow path becoming primed.

FIGS. 16a and 16b show another exemplary embodiment of an outlet plug 440 constructed in accordance with the present invention. The plug 440 of FIGS. 16a and 16b is similar to the plug 430 of FIGS. 9, 10a and 10b, such that similar elements have the same reference numeral. The outlet plug 440 of FIGS. 16a and 16b, however, includes an air removal filter having an outer layer 436a and an inner layer 436b. The inner layer 436b has predetermined physical properties, such as material pore size and/or thickness, that allows the inner layer 436b to expand to contact the outer layer 436a upon the flow path becoming substantially primed. The outer layer 436a of the air removal filter 440 is relatively transparent and the inner layer 436b is darker in coloring than the outer transparent layer 436a such that the inner layer 436b can be seen through the outer layer 436a when the inner layer contacts the outer layer. Alternatively, the flow restriction system can be provided with a sensor, such as a contact sensor, for providing a signal when the inner layer 436b contacts the outer layer 436a.

Figure 12:
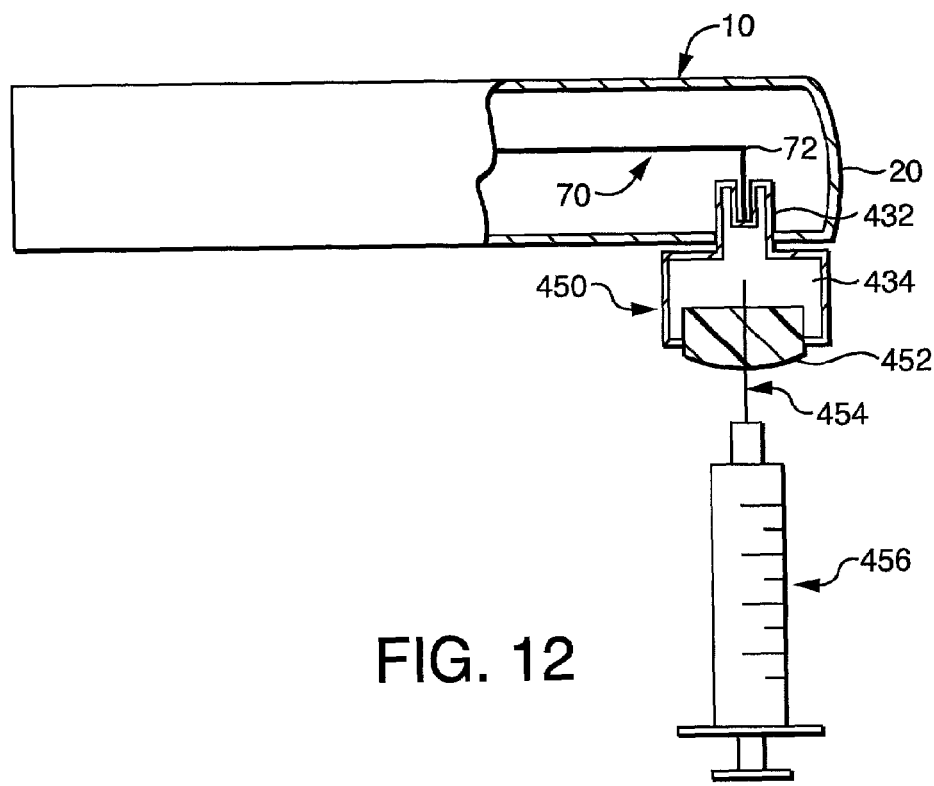
FIG. 12 is a side elevation view, partially cut-away, showing another exemplary embodiment of outlet plug constructed in accordance with the present invention, received on an exit port cannula of a fluid delivery device with a needle of a syringe inserted into the outlet plug for injecting fluid into the exit port cannula and the fluid delivery device.

FIG. 12 shows another exemplary embodiment of an outlet plug 450 constructed in accordance with the present invention. The plug 450 of FIG. 12 is similar to the plug 430 of FIGS. 9, 10a and 10b, such that similar elements have the same reference numeral. The outlet plug 450 of FIG. 12, however, includes an air removal filter 452 that is comprised of a material that also acts as a needle septum such that the exit port assembly 70 of the fluid delivery device 10 can also act as the fill port for the device 10. For example, FIG. 12 shows the air removal filter 452 receiving a needle 454 of a syringe 456 for filling the flow path of the device 10. The outlet plug 450, therefore, functions as an air removal filter, a flow restrictor and a needle septum. In this manner, the fluid delivery device 10 is further simplified since it does not require a separate fill port.

Figure 13:
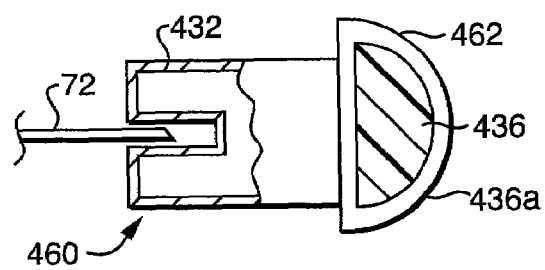
FIG. 13 is a side elevation view, partially cut-away, showing an additional exemplary embodiment of outlet plug constructed in accordance with the present invention, received on an exit port cannula.

FIG. 13 shows an additional exemplary embodiment of an outlet plug 460 constructed in accordance with the present invention. The plug 460 of FIG. 13 is similar to the plug 430 of FIGS. 9, 10a and 10b, such that similar elements have the same reference numeral. The outlet plug 460 of FIG. 13, however, includes a cap 462 further including straps 462a for securely holding the air removal filter 436 therein.

Figure 14:
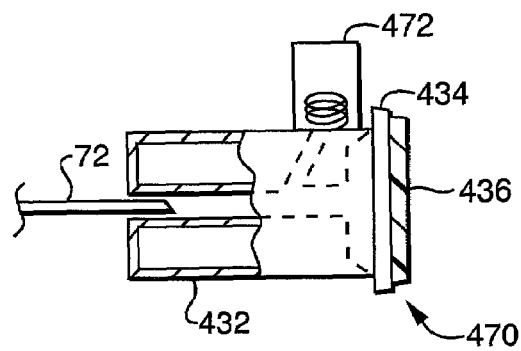
FIG. 14 is a side elevation view, partially cut-away, showing a further exemplary embodiment of outlet plug constructed in accordance with the present invention, received on an exit port cannula.

FIG. 14 shows still another exemplary embodiment of an outlet plug 470 constructed in accordance with the present invention. The plug 470 of FIG. 14 is similar to the plug 430 of FIGS. 9, 10a and 10b, such that similar elements have the same reference numeral. The outlet plug 470 of FIG. 14, however, further includes a pressure relief valve 472. The relief valve 472 ensures that pressure within the flow path of the fluid delivery device does not become excessive during a filling procedure, i.e., does not exceed a desired maximum level of flow path pressure, which could damage the fluid delivery device. Alternatively, the air removal filter 436 of the outlet plug can be adapted to allow fluid to pass out of the needle 72 upon a pressure within the flow path exceeding a desired maximum level of flow path pressure. The fluid leaking from the needle 72 would then act as a visual indication to a user that the fluid delivery device was improperly filled and should be discarded prior to use.

Figure 17:
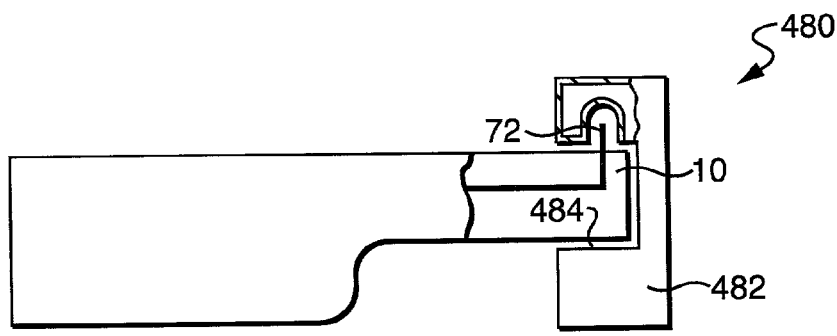
FIG. 17 is a side elevation view showing another exemplary embodiment of outlet plug constructed in accordance with the present invention, received on an exit port cannula of a fluid delivery device.

Referring now to FIG. 17, a further exemplary embodiment of an outlet plug 480 constructed in accordance with the present invention is shown. The plug 480 of FIG. 17 may be configured to act only as a flow restrictor (wherein the system would include a separate air removal filter within the flow path of the device 10) or may be configured to act as both the flow restrictor and the air removal filter. In any event, the outlet plug 480 of FIG. 17 also includes a handle 482 for supporting the fluid delivery device 10 during filling of the device through the fill port. The handle 482 of the outlet plug 480 preferably includes an outer contour 484 that nests with an outer contour of an end the fluid delivery device 10, as shown in FIG. 17.

Figure 18:
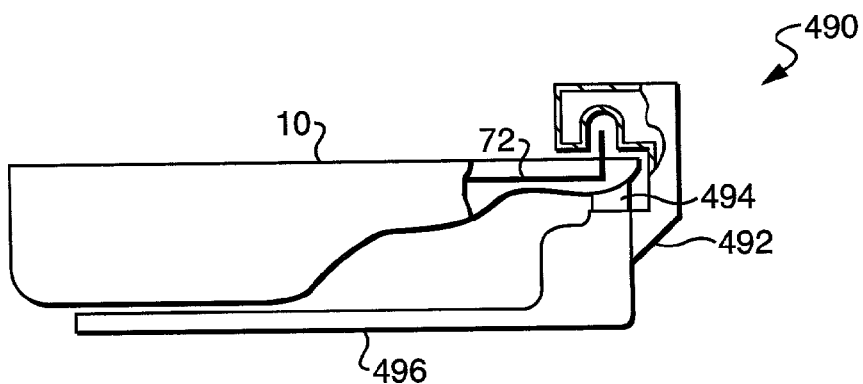
FIG. 18 is a side elevation view showing an additional exemplary embodiment of outlet plug constructed in accordance with the present invention, received on an exit port cannula of a fluid delivery device.

FIG. 18 shows another exemplary embodiment of an outlet plug 490 constructed in accordance with the present invention. The outlet plug 490 of FIG. 18 also includes a handle 492 for supporting the fluid delivery device 10 during filling of the device. The handle 492 of the outlet plug 490 includes an outer contour 494 that nests with an outer contour of an end of the fluid delivery device 10. The handle 494 also includes an extension 496 that supports a top surface of the fluid delivery device 10 during filling of the device.

Figure 19:
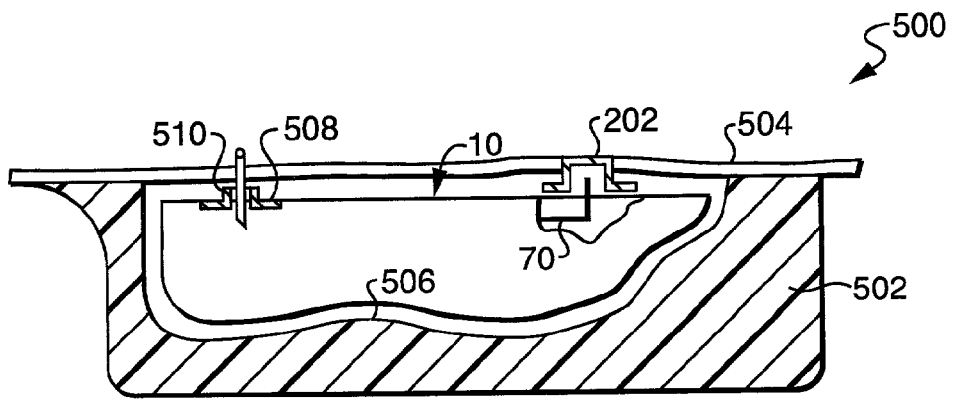
FIG. 19 is a side elevation view, partially cut-away, showing an exemplary embodiment of a package constructed in accordance with the present invention, and containing a fluid delivery device.

An exemplary embodiment of a packaging system 500 constructed in accordance with the present invention is shown in FIG. 19. The packaging system 500 includes a container 502 holding the fluid delivery device 10 (e.g., similar to the fluid delivery device 10 of FIGS. 2 through 4), and a protective cover 504 removably sealing the fluid delivery device 10 within the container 502. The container 502 includes an inner contour 506 that nests with an outer contour of the fluid delivery device 10 to provide support for the device 10 during handling and storage of the package system 500 and during filling of the device 10 by a user. The outlet plug 202 (e.g., similar to the outlet plug of FIGS. 2 through 4) of the flow restriction system is secured to and extends through the protective cover 504, so that the fluid delivery device 10 can be filled while the device 10 is still sealed in the container 502 and the cover 504. In addition, removal of the protective cover 504 from the container 502 removes the outlet plug 202 from the exit port assembly 70. The fluid delivery device 10 also includes a switch mechanism 508, and the protective cover 504 includes an insert 510 extending into the fluid delivery device 10 to normally hold the switch mechanism 508 open. Upon removal of the cover 504, the insert 510 is removed from the switch mechanism 508 such that the switch mechanism 508 can close. The switch mechanism 508 can be used, example, to turn on the processor of the fluid delivery device 10 just prior to the device 10 being attached to a patient.

Figure 20A:
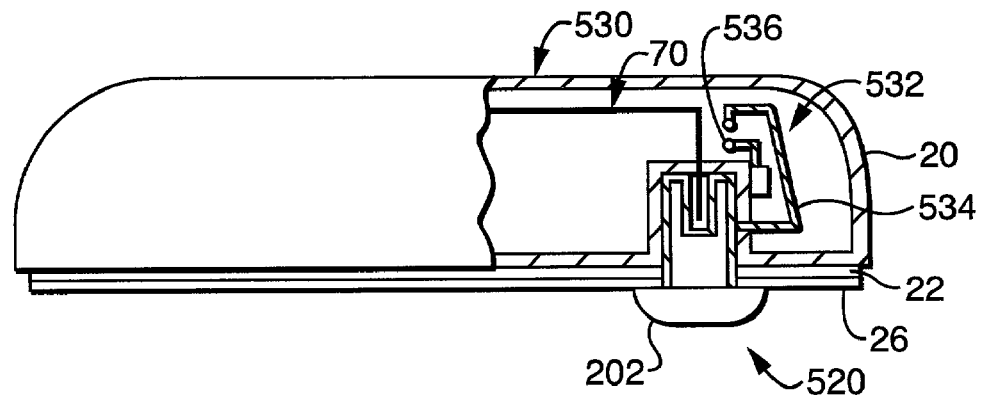
FIG. 20a is a side elevation view, partially cut-away, showing an exemplary embodiment of a fluid delivery device and an outlet plug constructed in accordance with the present invention.
Figure 20B:
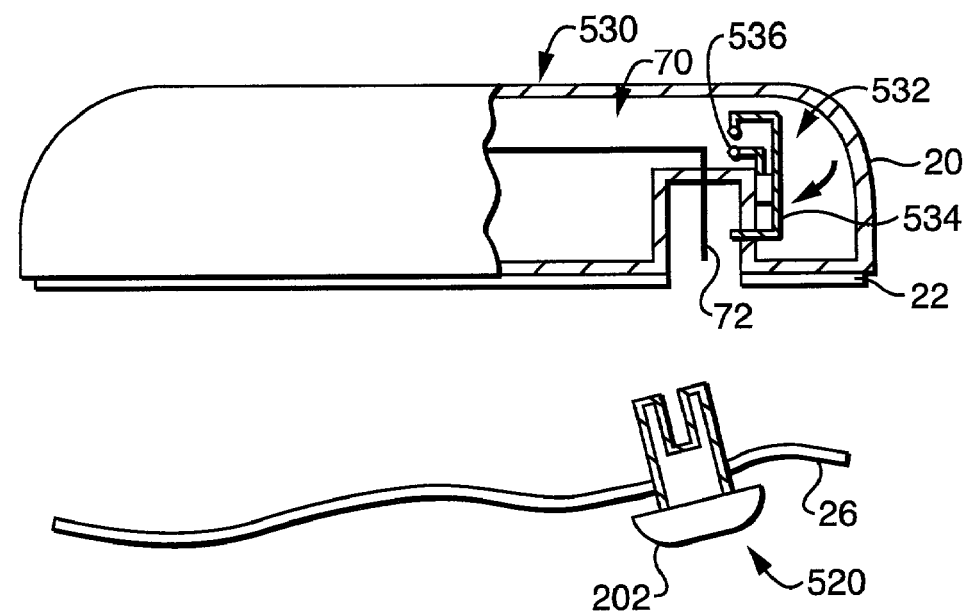

FIGS. 20a and 20b show yet a further exemplary embodiment of a flow restriction system 520 and a fluid delivery device 530 constructed in accordance with the present invention. The system 520 and the fluid delivery device 530 of FIGS. 20a and 20b are similar to the system 200 and the device 10 of FIGS. 2 through 4 such that similar elements have the same reference numeral.

The fluid delivery device 530 of FIGS. 20 and 20b includes an adhesive layer 22 on a bottom external surface of the housing 20 for securing the device 530 to a patient, and a removable protective layer 26 covering the adhesive layer 22 prior to attachment of the fluid delivery device 530 to a patient. The flow restriction system 520 includes an outlet plug 202 that acts as both a flow restrictor and an air removal filter for the system 520, and is secured to an insertable cannula 72 of the exit port assembly 70 prior to attachment of the fluid delivery device 530 to a patient. The outlet plug 202 is secured to the protective layer 26 of the fluid delivery device 530 so that the plug 202 is also removed from the cannula 72 when the protective layer 26 is removed from the adhesive layer 22 for attachment of the fluid delivery device 530 to a patient. FIG. 20a shows the protective layer 26 and the outlet plug 202 prior to removal from the fluid delivery device 530, while FIG. 20b shows the protective layer 26 and the outlet plug 202 after removal from the fluid delivery device 530.

The fluid delivery device 530 also includes a switch mechanism 532 for providing an indication when the outlet plug 202 is removed from the distal end of the cannula 72. The switch mechanism 532 can be connected, for example, to the processor (not shown) of the fluid delivery device 530 to provide an indication that the outlet plug 202 has been removed, or can be connected to an alarm, such as an LED, for providing an indication to a user that the outlet plug 202 has been removed. The switch mechanism 532 can also be used to turn on the fluid delivery device 530 (e.g., connect the power source to the processor) upon removal of the outlet plug 202.

In the exemplary embodiment shown in FIGS. 20a and 20b, the switch mechanism 532 includes a first lead 534 normally biased towards a second lead 536 to close the switch mechanism. The switch mechanism 532 is arranged and oriented with respect to the outlet port assembly 70 such that the outlet plug 202 pushes the first lead 534 away from the second lead 536 when the outlet plug 202 is positioned on the cannula 72, as shown in FIG. 20a. When the outlet plug 202 is removed from the distal end of the cannula 72, the first lead 534 is allowed to return to the second lead 536 and close the switch mechanism 532, as shown in FIG. 20b.

Figure 21:
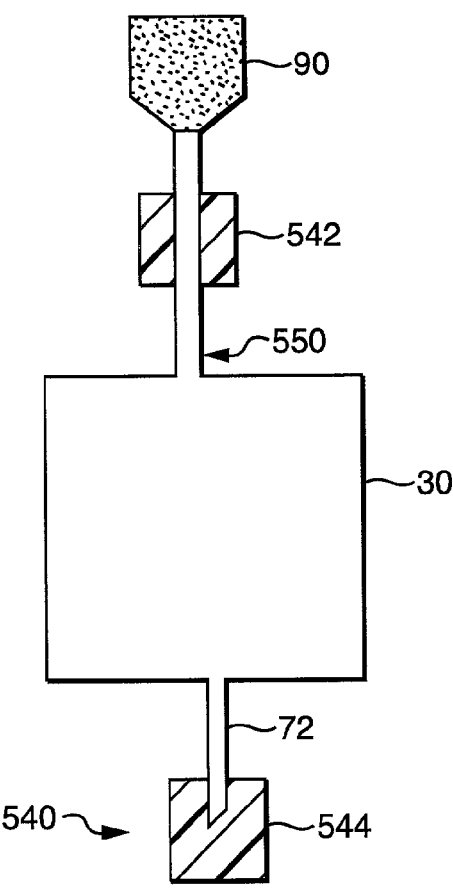
FIG. 21 is a representation of an exemplary embodiment of a flow path constructed in accordance with the present invention for use in a fluid delivery device.

Additional exemplary embodiments of a flow restriction system 540 and a flow path 550 of a fluid delivery device constructed in accordance with the present invention are shown in FIG. 21. The system 540 and the flow path 550 of FIG. 21 are similar to the system 200 and the flow path 12 of FIGS. 2 through 4 such that similar elements have the same reference numeral. The flow path 550 includes an outlet port assembly comprising a rigid cannula 72 (e.g., a needle with sharpened distal end), a reservoir 30 connected to the cannula 72, and a fill port comprising a needle septum 90 connected to the reservoir 30.

The flow restriction system 540 includes an air removal filter 542 positioned in the flow path 550 between the reservoir 30 and the fill port 90, and an outlet plug 544 removably fitted on the sharpened distal end of the rigid cannula 72. The outlet plug 544 is made of a suitable air removal filter material such that the outlet plug 544 functions as both an air removal filter and a flow restrictor. The outlet plug 544 causes an increased pressure within the flow path 550 during filling of the flow path through the fill port 90 (with a needle and syringe, for example), so that air can be effectively filtered through the air removal filter 542 and the outlet plug 544. The outlet plug 544 is removed from the cannula 72 prior to use of the flow path 530 (i.e., prior to injection of the cannula into a patient for delivery of fluid contained in the reservoir).

Figure 22:
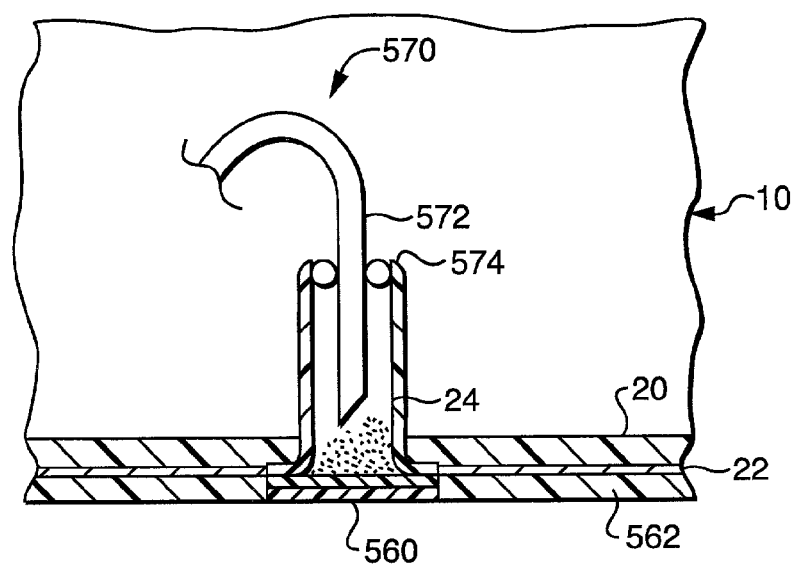
FIG. 22 is a side elevation view, partially cut-away, showing an exemplary embodiment of an exit port assembly and an outlet plug constructed in accordance with the present invention for use in a fluid delivery device.

FIG. 22 shows another exemplary embodiment of an outlet plug 560 constructed in accordance with the present invention. The outlet plug 560 is formed as part of a protective layer 562 removably attached to an adhesive layer 22 of the fluid delivery device 10. The exemplary embodiment of the fluid delivery device 10 of FIG. 22 includes an exit port assembly 570 having an injectable needle 572 for insertion into a patient. The needle 572 is extendable out of a port 24 in a housing 20 of the fluid delivery device 10. An o-ring 574 provides a fluid tight seal between the port 24 and the needle 572. The outlet plug 560 provides a substantially fluid-tight seal of the port 24 when the protective layer 562 is attached to the adhesive 22. The outlet plug 560 is made of a suitable air removal filter material such that the outlet plug 560 functions as both an air removal filter and a flow restrictor. In the embodiment shown, the outlet plug 560 is made of a different material than the remainder of the protective layer 562. The remainder of the protective layer 562 is made of a suitable material that readily detaches from the adhesive layer 22, such as wax paper or a plastic. Alternatively, the protective layer can be made entirely of a suitable air removal filter material that is also readily detachable from the adhesive layer 22, such that the portion of the protective layer positioned over the port 24 of the housing 20 can act as the outlet plug.

Figure 23:
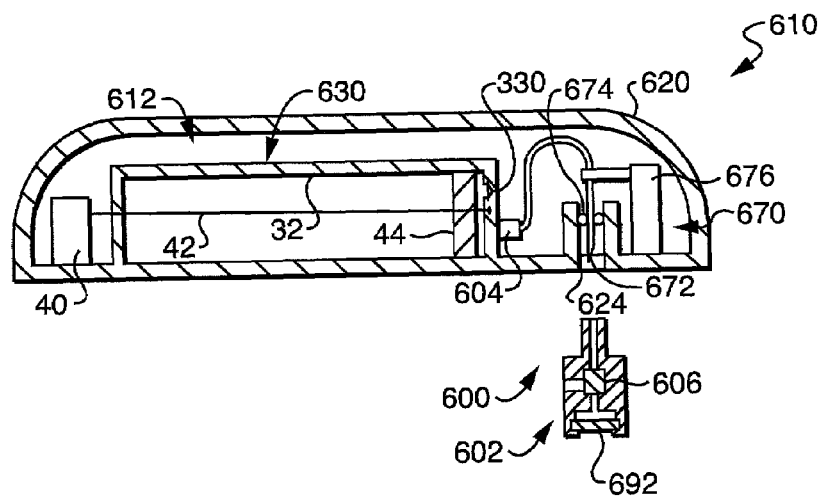
FIG. 23 is a sectional view showing an exemplary embodiment of a fluid delivery device and an outlet plug constructed in accordance with the present invention.
Figure 26:
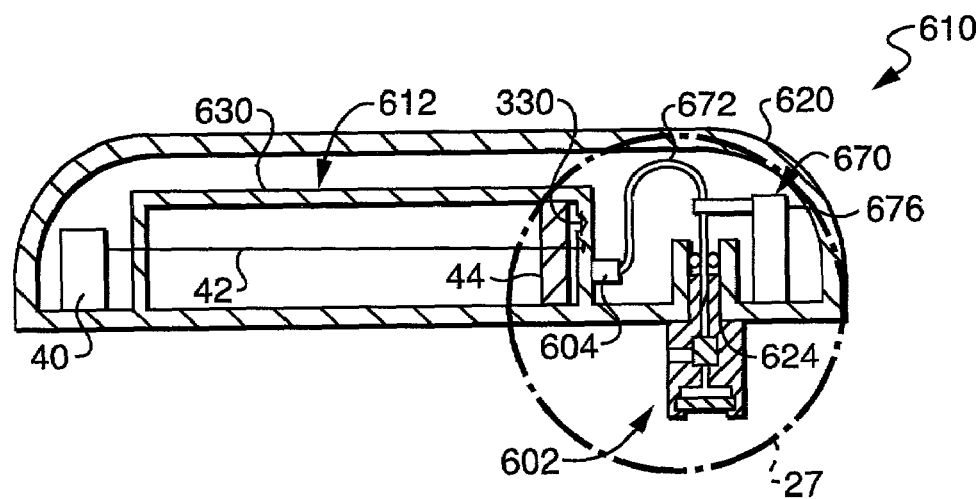
FIG. 26 is a sectional view showing the outlet plug of FIG. 23 attached to an exit port assembly of the fluid delivery device of FIG. 23.

FIGS. 23 and 26 show yet a further exemplary embodiment of a flow restriction system 600 and a fluid delivery device 610 constructed in accordance with the present invention. The system 600 and the fluid delivery device 610 of FIGS. 23 and 26 are similar to the system 200 and the device 10 of FIGS. 2 through 4 such that similar elements have the same reference numeral.

A flow path 612 of the fluid delivery device 610 includes a reservoir 630 and an outlet port assembly 670 terminating in a needle 672 for insertion into a patient. The needle 672 is extendable out of a port 624 in a housing 620 of the fluid delivery device 610. An o-ring 674 provides a fluid tight seal between the port 624 and the needle 672. The outlet port assembly 670 also includes an injection mechanism 676 for injecting the needle 672 into a patient. The flow path 612 does not require a separate fill port connected to the reservoir 630, as further discussed below.

Figure 24:
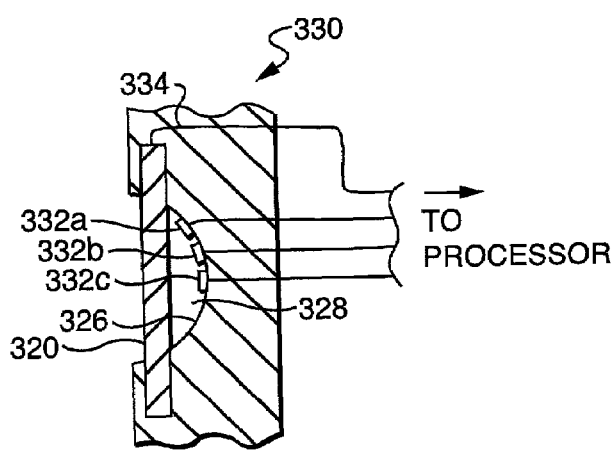
FIG. 24 is an enlarged sectional view of a pressure sensor of the fluid delivery device of FIG. 23.
Figure 27:
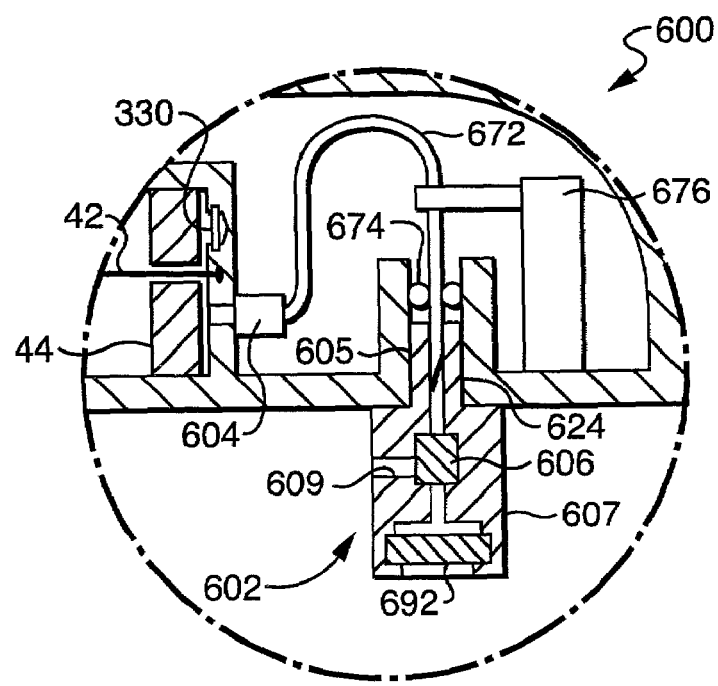
FIG. 27 is an enlarged sectional view of the outlet plug attached to the exit port assembly contained in circle 27 of FIG. 26.

The flow restriction system 600 includes an air removal filter and a flow restrictor combined in a single outlet plug 602 fitted to the end of the exit port assembly 670, as also shown in FIG. 27. The flow restriction system 600 further includes a flow sensor assembly 330 positioned at the end of the reservoir 630, as also shown in FIG. 24. A second air removal filter 604 is positioned between the reservoir 630 and the exit port assembly 670 and can be adapted to also function as a second flow restrictor if desired.

Figure 25:
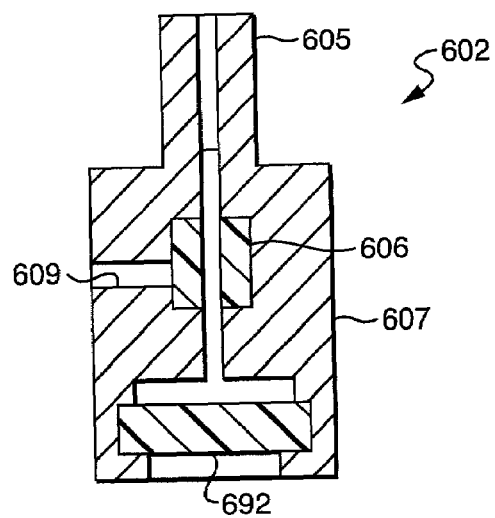
FIG. 25 is an enlarged sectional view of the outlet plug of FIG. 23.

The removable outlet plug 602 is fitted to the end of the exit port assembly 670 and prevents fluid leakage from the flow path 612 prior to use, e.g., during storage and during priming when filled by a user. The outlet plug 602 is removed by a user prior to attaching the fluid delivery device 610 to a patient's skin surface. Also referring to FIG. 25, the outlet plug 602 includes a sleeve 605 having a first end removably received in a substantially fluid-tight manner on the distal end of the needle 672, and a cap 607 connected to a second end of the sleeve 605. In the embodiment shown, the sleeve 605 and the cap 607 of the outlet plug 602 are unitarily formed from a resiliently flexible material. An air removal filter 606 is seated in the cap 607 such that air passing through the filter 606 can exit the outlet plug 602 through an air release port 609 in the cap 607. The air removal filter 606 also acts as the flow restrictor.

The outlet plug 602 further includes a needle septum 692. The outlet plug 602, therefore, functions as an air removal filter, a flow restrictor and a needle septum. In this manner, the fluid delivery device 610 is further simplified since it does not require a separate fill port.

As illustrated by the above described exemplary embodiments, the present invention generally provides a device for delivering fluid, such as insulin for example, to a patient. The device includes a flow path having an exit port assembly adapted to connect to a transcutaneous patient access tool (e.g., needle), and a reservoir connected to the exit port assembly. The device also includes a flow restriction system having an air removal filter communicating with the flow path and allowing air to exit the flow path and preventing fluid from exiting the flow path, and a flow restrictor positioned within the flow path between the air removal filter and the exit port assembly.

Among other features and advantages, the flow restriction system of the present invention allows the flow path of the fluid delivery device to be purged of air, or "primed" prior to operation, such that desired volumes of fluid can be accurately delivered by the device.

It should be understood that the embodiments described herein are merely exemplary and that a person skilled in the art may make variations and modifications to the embodiments described without departing from the spirit and scope of the present invention. All such equivalent variations and modifications are intended to be included within the scope of this invention as defined by the appended claims.

What is claimed is:

1. A device for delivering fluid to a patient, comprising:
   A) a flow path including,
      an exit port assembly adapted to connect to a transcutaneous patient access tool, and
      a reservoir connected to the exit port assembly; and
   B) a flow restriction system including,
      an air removal filter communicating with the flow path and allowing air to exit the flow path and preventing fluid from exiting the flow path, and
      a flow restrictor positioned within the flow path between the air removal filter and the exit port assembly,
   wherein the flow restrictor of the flow restriction system comprises an outlet plug removably connected to the exit port assembly to prevent fluid from exiting the flow path through the exit port assembly and the air removal filter of the flow restriction system comprises at least a portion of the outlet plug allowing air to exit the flow path through the exit port assembly;
   wherein the exit port assembly includes a transcutaneous patient access tool having a sharpened distal tip and the outlet plug is removably connected to the access tool; and
   wherein the reservoir includes a side wall extending towards an outlet connected to the exit port assembly, a plunger movably received within the side wall of the reservoir for forcing fluid through the outlet upon moving along the side wall, and wherein the device includes a dispenser for causing the plunger to move along the side wall of the reservoir, and a local processor connected to the dispenser and programmed to cause the dispenser to move the plunger based on flow instructions.

2. A device according to claim 1, wherein the dispenser includes an elongated shape memory element connected to the local processor and having a changeable length decreasing from an uncharged length to a charged length when at least one charge is applied to the shape memory element, the shape memory element connected to the plunger such that the changeable length of the shape memory element causes the plunger to move along the side wall of the reservoir.

3. A device according to claim 2, wherein the reservoir further includes:
   a threaded lead screw extending from the plunger and prevented from rotating about a longitudinal axis of the lead screw; and
   a rotatable gear threadedly engaging the threaded lead screw such that rotation of the gear in at least one direction causes longitudinal movement of the threaded lead screw and the plunger along the side wall of the reservoir towards the outlet of the reservoir; and
   the dispenser further includes a finger for engaging radially extending teeth of the gear, wherein the finger arid the teeth are adapted such that linear movement of the finger in a first direction adjacent the gear causes rotation of the gear while linear movement of the finger in a second direction adjacent the gear causes no rotation of the gear, and the elongated shape memory element is connected to the finger such that the changeable length of the shape memory element decreasing from an uncharged length to a charged length causes linear movement of the finger in one of the first and the second directions.

4. A device according to claim 3, wherein the dispenser further includes an actuation element connected to the finger for causing linear movement of the finger in the first direction.

5. A device according to claim 4, wherein the actuation element comprises a spring.

6. A device for delivering fluid to a patient, comprising:
   A) a flow path including,
      an exit port assembly adapted to connect to a transcutaneous patient access tool, and
      a reservoir connected to the exit port assembly; and
   B) a flow restriction system including,
      an air removal filter communicating with the flow path and allowing air to exit the flow path and preventing fluid from exiting the flow path, and
   a flow restrictor positioned within the flow path between the air removal filter and the exit port assembly,
   wherein
      the reservoir includes a side wall extending towards an outlet connected to the exit port assembly, a plunger movably received within the side wall of the reservoir for forcing fluid through the outlet upon moving along the side wall, and wherein the device includes a dispenser for causing the plunger to move along the side wall of the reservoir, and a local processor connected to the dispenser and programmed to cause the dispenser to move the plunger based on flow instructions, and
      the dispenser includes an elongated shape memory element connected to the local processor and having a changeable length decreasing from an uncharged length to a charged length when at least one charge is applied to the shape memory element, the shape memory element connected to the plunger such that the changeable length of the shape memory element causes the plunger to move along the side wall of the reservoir.

7. A device according to claim 6, wherein the reservoir further includes:
   a threaded lead screw extending from the plunger and prevented from rotating about a longitudinal axis of the lead screw; and
   a rotatable gear threadedly engaging the threaded lead screw such that rotation of the gear in at least one direction causes longitudinal movement of the threaded lead screw and the plunger along the side wall of the reservoir towards the outlet of the reservoir; and
   the dispenser further includes a finger for engaging radially extending teeth of the gear, wherein the finger and the teeth are adapted such that linear movement of the finger in a first direction adjacent the gear causes rotation of the gear while linear movement of the finger in a second direction adjacent the gear causes no rotation of the gear, and the elongated shape memory element is connected to the finger such that the changeable Length of the shape memory element decreasing from an uncharged length to a charged length causes linear movement of the finger in one of the first and the second directions.

8. A device according to claim 7, wherein the dispenser further includes an actuation element connected to the finger for causing linear movement of the finger in the first direction.

9. A device according to claim 8, wherein the actuation element comprises a spring.

* * * * *